(12) United States Patent
Jokinen et al.

(10) Patent No.: US 9,949,922 B2
(45) Date of Patent: Apr. 24, 2018

(54) SILICA HYDROGEL COMPOSITE

(71) Applicant: DELSITECH OY, Turku (FI)

(72) Inventors: Mika Jokinen, Turku (FI); Harry Jalonen, Turku (FI); Ari-Pekka Forsback, Turku (FI)

(73) Assignee: DelSiTech Oy, Turku (FI)

( * ) Notice: Subject to any disclaimer, the term of this patent is extended or adjusted under 35 U.S.C. 154(b) by 24 days.

(21) Appl. No.: 14/896,612

(22) PCT Filed: Jun. 18, 2014

(86) PCT No.: PCT/FI2014/050492
§ 371 (c)(1),
(2) Date: Dec. 7, 2015

(87) PCT Pub. No.: WO2014/207304
PCT Pub. Date: Dec. 31, 2014

(65) Prior Publication Data
US 2016/0136088 A1 May 19, 2016

(30) Foreign Application Priority Data
Jun. 24, 2013 (FI) .................................... 20135685

(51) Int. Cl.
| | | |
|---|---|---|
| A61K 9/16 | (2006.01) | |
| A61K 9/00 | (2006.01) | |
| A61K 9/14 | (2006.01) | |
| A61K 9/19 | (2006.01) | |
| A61K 31/455 | (2006.01) | |
| A61K 49/00 | (2006.01) | |

(52) U.S. Cl.
CPC ............ *A61K 9/0024* (2013.01); *A61K 9/143* (2013.01); *A61K 9/1611* (2013.01); *A61K 9/19* (2013.01); *A61K 31/455* (2013.01); *A61K 49/0073* (2013.01)

(58) Field of Classification Search
CPC ............................ A61K 9/0019; A61K 9/0024
See application file for complete search history.

(56) References Cited

U.S. PATENT DOCUMENTS

| | | | | |
|---|---|---|---|---|
| 2006/0148633 A1* | 7/2006 | Kuhn | .................... | C04B 28/005 501/1 |
| 2007/0275068 A1* | 11/2007 | Martens | .................. | C01B 33/18 424/484 |
| 2009/0324695 A1 | 12/2009 | Ducheyne et al. | ........... | 424/445 |

FOREIGN PATENT DOCUMENTS

| | | |
|---|---|---|
| EP | 0 906 243 | 12/1997 |
| KR | 20100060931 | 6/2010 |
| WO | 2005/082781 | 9/2005 |
| WO | WO 2007/135224 | 11/2007 |
| WO | WO 2008/104635 | 9/2008 |
| WO | WO-2008104635 A1 * | 9/2008 ........... A61K 9/0019 |
| WO | WO 2011/038485 | 4/2011 |

OTHER PUBLICATIONS

Yu et al., "Mesoporous SBA-15 Molecular Sieve as a Carrier for Controlled Release of Nimodipine," 123 *Microporous and Mesoporous Materials* 298 (2009).
Barbe et al., "Silica Particles: A Novel Drug-Delivery System," 16 *Adv. Mater.* 1959 (2004).
Lu et al., "Mesoporous Silica Nanoparticles as a Delivery System for Hydrophobic Anticancer Drugs," 3 *Small* 1341 (2007).
Holland et al., "Transforming Growth Factor-B1 Release From Oligo(poly(ethylene glycol)fumerate) Hydrogels in Conditions That Model the Cartilage Wound Healing Environment," 94 J. Controlled Release 101 (2004).
Holland et al., "In Vitro Release of Transforming Growth Factor-B1 From Gelatin Microparticles Encapsulated in Biodegradable, Injectable Oligo(poly(ethylene glycol)fumerate) Hydrogels," 91 J. Controlled Release 299 (2003).
Holland et al., "Dual Growth Factor Delivery From Degradable Oligo(poly(ethylene glycol)fumerate) Hydrogel Scaffolds for Cartilage Tissue Engineering," 101 J. Controlled Release 111 (2005).
Park et al., "Delivery of TGF-B1 and Chondrocytes Via Injectable, Biodegradable Hydrogels for Cartilage Tissue Engineering Applications," 26 Biomaterials 7095 (2005).
Stanwick et al., "Enhanced Neurotrophin-3 Bioactivity and Release From a Nanoparticle-loaded Composite Hydrogel," 160 J. Controlled Release 666 (2012).
Caicco et al., "A Hydrogel Composite System for Sustained Epi-Cortical Delivery of Cyclosporin A to the Brain for Treatment of Stroke," 166 J. Controlled Release 197 (2013).
Shen et al., "Accelerated In Vitro Release Testing of Implantable PLGA Microsphere/PVA Hydrogel Composite Coatings," 422 Int'l J. Pharmaceutics 341 (2012).
Wang et al., "A pH-Sensitive Molecularly Imprinted Nanospheres/Hydrogel Composite as a Coating for Implantable Biosensors," 31 Biomaterials 4944 (2010).
Gupta et al., "Fast-gelling Injectable Blend of Hyaluronan and Methylcellulose for Intrathecal, Localized Delivery to the Injured Spinal Cord," 27 Biomaterials 2370 (2006).
Viitala et al., "Adjustably Bioresorbable Sol-Gel Derived SiO2 Matrices for Release of Large Biologically Active Molecules," 36 J. Sol-Gel Sci. Tech. 147 (2005).
Viitala et al., "Chemical Characterization of Bioresorbable Sol-Gel Derived SiO2 Matrices Prepared at Protein-compatible pH," 351 J. Non-Crystalline Solids 3225 (2005).
Viitala et al., "Mechanistic Studies on Release of Large and Small Molecules From Biodegradable SiO2," 336 Int'l J. Pharmaceutics 382 (2007).

* cited by examiner

*Primary Examiner* — Micah Paul Young
(74) *Attorney, Agent, or Firm* — James C. Lydon

(57) ABSTRACT

This invention relates to a silica hydrogel composite obtainable by mixing silica particles, comprising an encapsulated agent, with a silica sol, wherein obtained hydrogel composite is shear-thinning. The present invention also relates to use of the silica hydrogel composite according to the invention for an injectable, flowing or extrudable formulation. The present invention further relates to a method for preparing the silica hydrogel.

23 Claims, 10 Drawing Sheets

SILICA HYDROGEL COMPOSITE

FIELD OF THE INVENTION

This invention relates to a silica hydrogel composite. More specifically this invention relates to a silica hydrogel composite comprising an encapsulated agent and the silica hydrogel composite is feasible for drug delivery.

BACKGROUND OF THE INVENTION

The publications and other materials used herein to illuminate the background of the invention, and in particular, cases to provide additional details respecting the practice, are incorporated by reference.

In drug delivery, the "burst effect" or "burst release", in which a large amount of a drug is quickly released (and typically immediately upon placement into release medium) from a pharmaceutical formulation (typically consisting of a drug or an active pharmaceutical ingredient (API) and a matrix material with optional additives), is mostly considered to be harmful, even dangerous if the concentration of a drug in the body would increase too much. If the pharmaceutical formulation is in the form of a device and the released amount in the burst is high, it may also reduce the lifetime of the device remarkably. However, if the ratio between the drug released in the burst and the total amount of the drug is low, and the burst can be controlled by the formulation, the burst may also be beneficial. For treatment of some diseases it may better to have higher drug concentrations in the beginning of the treatment, which should be followed by a controlled and sustained release. However, a controlled burst in the beginning of the medication is not often needed, because in the beginning of a treatment, e.g., while implanting or injecting the release-controlling pharmaceutical formulation, it is relatively easy to give a certain amount of a drug also orally or by injecting a suitable amount of a drug solution. Thus, in most cases the burst is to be avoided instead a controlled and sustained release is desired from the very beginning, and most preferably a zero order release.

The key question is that the burst effect should be controlled. If the burst is not desired, there should be a method to avoid or minimize it. There are various materials and methods (e.g., coatings, membranes, pore size modifications, reservoir structures with different outer layer properties, chemical surface modifications, surface erosion-controlled biodegradation) developed to control it, because there are several reasons for the burst. The burst may depend, e.g., on the drug properties (e.g., a highly water-soluble drug may be released fast from a matrix that otherwise controls very well a less water-soluble drug), the typical matrix pore structure may be more beneficial for certain size classes of drugs (e.g., for macromolecules such as proteins), the (pore) surface of the matrix or a membrane may have different interaction forces with different drugs, and the preparation process (e.g., methods with sudden phase transformations such as spray-drying) of the formulation may typically result in a structure, where a certain, and relatively large amount (larger than the average in the matrix) of a drug is often located near the outer surface of the matrix material.

The burst is more difficult to control when the encapsulated molecule is highly water-soluble and it becomes somewhat easier for larger molecules and other large agents, e.g., viral vector, but the burst depends often also on the drug loading in a pharmaceutical formulation, i.e. a high weight ratio between a drug and a matrix material controlling the release. It is obvious in most cases that the lower the drug concentration the easier it is to control the burst and sustained release. Lower drug concentrations do not affect the (formation of) matrix structure so much and also the accumulation of a large amount of a drug near the outer surface of the matrix material is less probable. However, the high drug loading capability is often desired, because it provides flexibility in the product development and it is easier to develop controlled release matrices also for less potent drugs. The high drug loading enables also smaller size for controlled delivery systems, e.g., smaller implant or a smaller volume and dry content in an injectable system. The reduced size or amount is preferable because the administration is easier and it also improves the patient compliance.

Materials and methods for burst control are often drug-dependent and there is a need for a more general solution that would fit several different active pharmaceutical ingredients (API) and other therapeutic and biologically active agents. Hydrogels are potential solutions when combined with other morphologies, e.g., with particles of different size such as nanoparticles or microparticles. The resulting structures can be adjusted to be injectable with thin needles to obtain minimally invasive administration solutions. If the interaction between the particles and the hydrogel is strong enough or if the combined structure otherwise results in a unique structure, it may in the best case result in a structure that controls the release (whole release and/or burst) of API and other therapeutic and biologically active agents independently on the encapsulated agent, e.g., independent of the water solubility, hydrophobicity or other properties. Although the release would not totally be independent of the properties of API or other therapeutic and biologically active agents, the combined structure of particles and hydrogels may still have a major impact on the release kinetics and may solve problems, such as too fast burst in the beginning of the release.

US2009/0324695 by Ducheyne and Devore discloses a combination of organic hydrogels and silica microparticles in the adjustment of drug release kinetics and in controlling burst. They disclose a material that turns into a hydrogel when used (e.g., when placed into contact with tissue and the fluids of the tissue), i.e., the disclosed product is not a hydrogel. The weight ratio between the polymer used to prepare the hydrogel and silica varies between 5-95%.

Holland et al. (Journal of Controlled Release, 91 (3), p. 299-313, 2003; Journal of Controlled Release, 94 (1), p. 101-114, 2004; Journal of Controlled Release, 101 (1-3), p. 111-125, 2005 and Biomaterials, 26 (34), p. 7095-7103, 2005) have combined organic microparticles and organic polymers to prepare an injectable formulation. They have focused on a large encapsulated agents (growth factor proteins that are macromolecules) and they have combined organic materials (gelatine microparticles and oligo(poly (ethylene glycol) fumarate, OPF). The combined composition of gelatine microparticles and OPF reduced the burst of growth factors, but either increased or decreased the overall release rate of the growth factors when compared with the gelatin microparticles as such.

Shoichet et al. (Journal of Controlled Release, 160, p. 666-675, 2012 and Journal of Controlled Release, 166, p. 197-202, 2013) combined organic PLGA nanoparticles with organic hyaluronan (1 wt-%, 2600 kDa) and methyl cellulose (3 wt-%, 300 kDa) (HAMC) or organic PEG-400 to form composite formulations (whether they are injectable or not is not mentioned). The combination affected both the burst and the overall release when compared with the particles as such.

Shien and Burgess (International Journal of Pharmaceutics, 422, p. 341-348, 2012) have combined organic PLGA microparticles with an organic PVA hydrogel. They prepared and implantable device (after hydrogel formation, several freezing-thawing cycles were conducted) and they did not compare the release properties to the PLGA microparticles as such. Hence, no benefit of the combination was shown, not on the burst or on the overall release.

Wang et al. (Biomaterials, 31, p. 4955-4951, 2010) have combined organic nanospheres (HEMA-DEAMEA-EGDMA) with an organic hydrogel (HEMA-MPC-TMPTA-PEGDA) to prepare an implantable material (the hydrogel was freeze-dried into an implant). The composite did not affect the burst, but reduced the overall release rate.

Gupta et al. have prepared an injectable, shear-thinning hydrogel out of blends of hyaluronan and methylcellulose (HAMC).

OBJECT AND SUMMARY OF THE INVENTION

One object of the present invention is to provide a silica hydrogel composite with an encapsulated agent.

Another object of the present invention is to provide use for the silica hydrogel composite with an encapsulated agent.

A further object of the present invention is to a silica hydrogel composite with an encapsulated agent for medical use.

A still further object of the present invention is to provide a method for preparing the silica hydrogel composite with an encapsulated agent.

The present invention provides a silica hydrogel composite obtainable by mixing a) silica particles, comprising an encapsulated agent other than the silica itself and having a maximum diameter of ≤1 000 μm, as such or as a suspension, with b) a silica sol;

wherein i) said silica sol has a solid content of ≤5 wt-%, ii) said silica hydrogel composite comprises up to 85 wt-% of said silica particles, and iii) said hydrogel composite is shear-thinning. The present invention also provides a use of the silica hydrogel composite according to the invention for an injectable, flowing or extrudable formulation.

The present invention also provides use of a silica hydrogel composite according to the present invention for an injectable formulation.

The present invention further provides a silica hydrogel composite of the invention for administering an encapsulated agent.

The present invention still further provides a method for preparing a silica hydrogel composite wherein silica particles, comprising a biologically active agent other than the silica itself and having a maximum diameter of ≤1 000 μm, as such or as a suspension, are mixed with a silica sol; wherein i) said silica sol has a solid content of ≤5 wt-%, ii) said hydrogel composite comprises up to 85 wt-% of said silica particles, and iii) said hydrogel composite is shear-thinning.

DETAILED DESCRIPTION OF THE INVENTION

Figure 1:
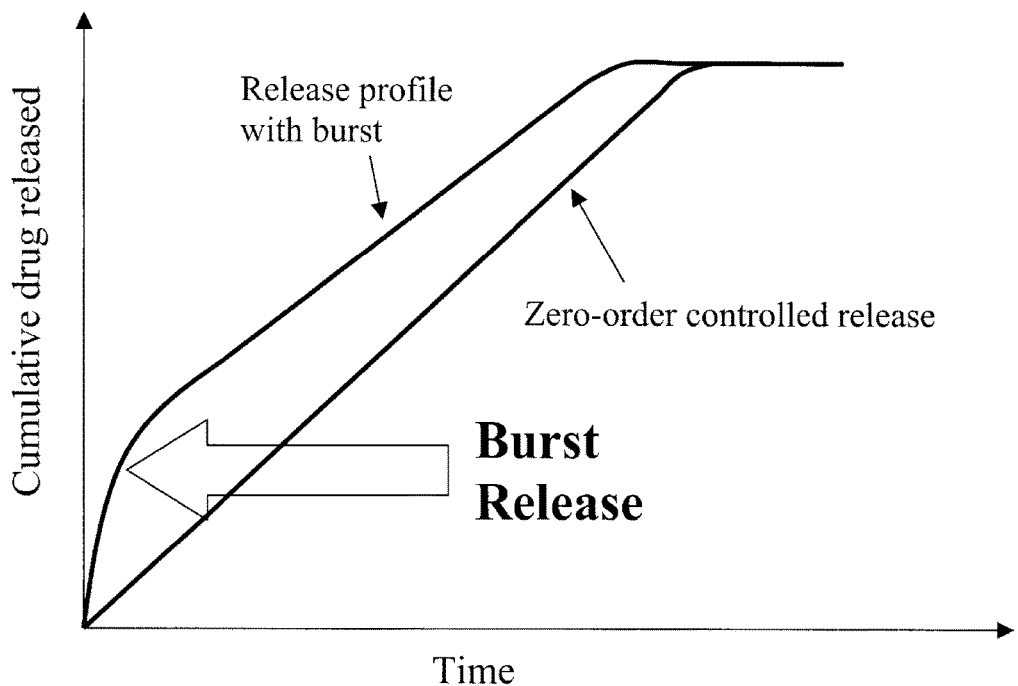
FIG. 1 illustrates burst release.

The gist of the invention is in that burst release of an encapsulated agent from silica particles can surprisingly be eliminated or highly reduced by preparing a silica hydrogel composite from the silica particles and a silica sol without essentially affecting the release rate of the encapsulated agent after eliminated burst release.

Terms

Gel should be understood in the context of this application to be a homogeneous mixture of at least one solid phase and one liquid phase, i.e., a colloidal dispersion, where solid phase(s), e.g. silica as such and/or as partly or fully hydrolysed, is the continuous phase and the liquid(s), e.g. water, ethanol and residuals of silica precursors, is homogeneously dispersed in the structure. The gel is viscoelastic and the elastic properties dominate, which is indicated by rheological measurements under small angle oscillatory shear that the elastic modulus, G' is greater than the viscous modulus, G". In the context of this invention G' is preferably <100×G"; more preferably G'>3×G" and/or <30×G"; most preferably G'>5×G" and/or <10×G".

Injectable Gel in a context of this application is a rheological property of a composition. Before injection, e.g. as stored in a syringe and/or in an aluminium foil at temperatures <37° C., e.g., at room temperature (at 20-25° C.) or in a refrigerator (at 4-8° C.), the composition is a gel, i.e., the elastic modulus (measured under small angle oscillatory shear) G' is greater than the viscous modulus G" and preferably G'<10×G". Typically G' is <300 kPa, preferably <100 kPa and most preferably <30 kPa. When shear stress is applied on the injectable gel, e.g. by injecting the injectable gel from a syringe through a thin needle (e.g., 18-25 G: the outer diameter of 25 G is 0.5 mm, the inner diameter varies, it is commonly ≤0.24 mm; the outer diameter of 18 G is 1.27 mm, the inner diameter varies, it is commonly ≤0.84 mm) it turns into a flowing form, which is indicated in a shear-thinning behaviour (clearly decreasing dynamic viscosity with increasing shear rate, e.g. 10-100-fold decrease in dynamic viscosity with 100-fold increase in the shear rate) in rotational measurements with a rheometer. When the shear stress ends, e.g. after injection with the thin needle, the injectable gel is again a gel, non-flowing and the elastic modulus, G' is larger than the viscous modulus, G".

The hydrogel should be understood to be a gel, where the liquid phase is water or water-based containing more than 50 weight-% (wt-%) of water. Typically the liquid phase of the hydrogel comprises >65 wt-%, more typically >90 wt-% and most typically >95 wt-% of water. The liquid phase can additionally comprise other liquids, typically organic solvents, e.g. ethanol. Typically the concentration of such solvents, e.g. ethanol, is <10 wt-%, more typically <3 wt-% and most typically <1 wt-%. In the context of this invention the composite of the invention is considered a hydrogel since it fulfils the basic criteria of a hydrogel. Accordingly, when referring to the hydrogel of the invention this referral is equivalent to a referral to the composite of the invention. In the context of this invention the silica hydrogel composite of the invention preferably comprises 20 to 70 wt-%, more preferably 30 to 60 wt-%, and most preferably 40 to 55 wt-% of water.

The sol should be understood to be a homogeneous mixture of at least one liquid phase and one solid phase, i.e., a colloidal dispersion, where the liquid phase(s), e.g. water, ethanol and residuals of silica precursors, is the continuous phase and the solid phase(s), e.g. colloidal particles of silica and/or as partly or fully hydrolysed silica and/or aggregates of said particles are homogeneously dispersed in the said liquid phase characterized in that the sol has clear flow properties and the liquid phase is dominating. A suspension can also be called a sol especially if the solid particles are colloidal, being smaller than 1 μm in diameter. In the context of the present invention, however, the term sol refers to a colloidal dispersion wherein the solid particles are ≤50 nm and the term suspension refers to a dispersion wherein the solid particles are >50 nm.

The term sol-gel transfer refers to a process where a sol turns to a gel. The most typical example on a preparation process comprising a sol-gel transfer is as silica and other corresponding materials, such as $TiO_2$ and $ZrO_2$ are synthesised from liquid phase precursors, typically alkoxides, alkylalkoxides, aminoalkoxides and inorganic precursors, such as silicate solutions that form after hydrolysis and condensation first particles, which turns the system to a sol, after which the particles aggregate and/or grow in size and the sol turns to a gel either spontaneously (typically in acidic sols) or by induced changes, such as pH change or salt addition (typically in alkaline sols). In the said example on alkoxides and silicate solutions, the sol-gel transfer occurs as a part of the above described longer process, which is often called a sol-gel process. The term sol-gel process is also commonly used for the preparation of powder of colloidal particles, where the alkaline sols does not actually form a gel, but the liquids in the sol are evaporated resulting in the powder. However, the sol-gel transfer may also occur for ready-made silica powders or other ceramic powders, such as oxide powders, e.g. $SiO_2$, $TiO_2$, $ZrO_2$, $Al_2O_3$. The powders may have been prepared by any method; also mined powders can be used as such or as modified (e.g. as ground and washed). The sol-gel transfer for the ready-made powders is possible especially for powders that consist of colloidal particles (diameter ca. 5 micrometers or below), i.e., as a colloidal powder is mixed with a liquid, e.g. water it can form a stable suspension, i.e., a sol and it may spontaneously form a gel as the silica particles are hydrolysed in water and at least partial condensation of hydroxyl groups and/or particle aggregation occur(s) or it can be further flocculated/coagulated to a gel, e.g. by adjusting pH and/or adding salt and/or other substances that affect the stability, such as other liquids or an additional silica sol.

The term sol-gel derived silica refers to silica prepared by the sol-gel process wherein the silica is prepared from liquid phase precursors, such as alkoxides, alkylalkoxides, aminoalkoxides or inorganic silicate solutions, which by hydrolysis and condensation reactions form a sol that turns to a gel or forms a stable sol. The liquids in the stable silica sol can be evaporated, which results in the formation of a powder consisting typically of colloidal silica particles. The resulting gels/particles can be optionally aged, dried and heat-treated and if heat-treated, preferably below 700° C. The sol-gel derived silica prepared below 700° C. is commonly amorphous. The sols can be let to gel in a mould for form-giving. The sol-gel derived silica can also be prepared by processing to different morphologies by simultaneous gelling, aging, drying and formgiving, e.g. by spray-drying to microparticles, by dip/drain/spin-coating to films, by extrusion to monolithic structures or by spinning to fibres.

Gel point shall be understood to mean the time point when the sol that is flowing turns to a gel that is viscoelastic and the elastic properties dominate, which is indicated by rheological measurements under small angle oscillatory shear that the elastic modulus, G' is greater than the viscous modulus. The viscoelastic properties are commonly measured with a rheometer (a measuring device for determination of the correlation between deformation, shear stress and time) by the oscillatory shear, where shear stresses are small (small angles of deformation). The total resistance in small oscillatory shear is described by the complex modulus (G*). The complex modulus contains two components: 1) elastic modulus, also called storage modulus, G' that describes that material has some elastic properties that are characteristic for a solid material, i.e., the gel system will gain energy from the oscillatory motion as long as the motion does not disrupt the gel structure. This energy is stored in the sample and is described by elastic modulus; 2) viscous modulus, also called loss modulus, G" that describes flow properties, i.e., a system, e.g. a silica sol that will in an oscillatory shear create motion between the ingredients of the sol describing the part of the energy, which is lost as viscous dissipation. As G*=G' a material is called elastic and as G*=G" a material is called viscous. At the gel point, the elastic modulus, G' becomes larger than the viscous modulus, G". As G'>G", a viscoelastic material is called semi-solid and correspondingly as G">G, a viscoelastic material is called semi-liquid. The magnitude of the elastic and viscous modulus depends on the shear stress, which depends on the applied strain (small angle deformation) and frequency (of the oscillatory shear). The measurements are conducted by ensuring an adequate signal for a specific measuring system, i.e., a strain sweep is commonly done at constant frequencies to find the proper signal and the linear viscoelastic region for the rheometer system and then the actual measurements are done at constant strain with varying frequency. The varying frequencies give varying elastic and viscous modulus and the measurement show whether the solid or liquid phase dominates. It is also typical that the elastic modulus increases fast after the gel point if the surrounding conditions are not significantly changed, e.g. 100-700 fold increase in G' within few minutes after the gel point is typical for gels formed from acidic sols near room temperature, e.g. for a R15 sol at pH=2 that turns to a gel (R=water-to-alkoxide molar ratio). For larger R-values, such as R150 and R400, the elastic modulus, G' remains on a low level even after the gel point and increase of G' is not fast, which makes it possible to have gel structures that remain injectable with thin needles. In the form of a gel after the defined gel point, the solid state dominates, but the system still contains varying amounts of liquids and the material is typically soft and viscoelastic before drying, and hard and brittle if it is extensively dried. In the form of a sol, the liquid state dominates, but the system contains varying amounts of solid phase(s) and the system is still flowing. Before the gel point it is typical that a steep increase in dynamic viscosity and elastic modulus is observed, which continues to rise after the gel point as the structure is developing. In the context of the present invention gel point of the composite of the invention has been reached prior to obtaining the injectable gel of the invention.

Injectable means, in the context of this invention, administrable via a surgical administration apparatus, e.g. a needle, a catheter or a combination of these.

Shear-thinning in the context of this application is a rheological property of a composition. Whenever the shear stress or shear rate of such a composition is altered, the composition will gradually move towards its new equilibrium state and at lower share rates the shear thinning composition is more viscous than newtonian fluid, and at higher shear rates it is less viscous. Thus shear-thinning refers to an effect where a fluid's viscosity, i.e. the measure of a fluid's resistance to flow, decreases with an increasing rate of shear stress.

In the context of the invention the term linear viscoelastic region refers to that measurement is carried out employing small oscillatory shear selecting the strain (deformation) so that the material is not at all, or is only minimally, disrupted. To determine the linear viscoelastic region, a strain sweep test at constant frequency is done by increasing the amplitude incrementally. The maximum strain to be used in the oscillatory measurements (conducted within the linear viscoelastic region) is typically selected so that the elastic modulus decreases less than 5% compared with the storage modulus at lowest amplitude in the sweep.

Silica particles refers in the context of the present invention to particles of silica prepared by spray drying or liquid phase synthesis, by chopping spun or drawn silica fibres, by moulding or casting silica monoliths and, when necessary for obtaining defined particle size, by crushing moulded or cast silica monoliths. In the context of the present invention liquid phase synthesis refers to e.g. emulsion polymerisation, sol-gel method or molecular self-assembly. Silica particles of the present invention are ≤1 000 μm in diameter as defined by laser diffraction methodology, e.g. employing the Malvern Mastersizer MicroPlus particle size analyser (Malvern Instruments) according to example 7. Particle sizes referred to in the context of the present invention are, as well, as defined by laser diffraction methodology. Silica refers in the context of the present invention preferably to amorphous silica as such, amorphous silica containing water, fully or partly hydrolysed amorphous silica or silica in water-dissolved form, such as silicic acid.

R-values referred to in the application, especially in the examples, are defined by the water-to-alkoxide molar ratio of the recipes. Silica compositions may also be expressed with 2 R-values, e.g., R6-50, where 6 is the initial molar ratio that is used and 50 correspond to the total molar water-to-alkoxide ratio after addition of extra water (or other liquid, such as ethanol in a the same volume that would correspond to the volume of water needed for water-to-alkoxide ratio 50) during some stage of the preparation.

The burst or burst release should be understood to be the amount of the encapsulated agent released (in/into tissue, tissue/body fluids, simulated body/physiological/tissue fluids) in the beginning of the release. Depending on the context, i.e. whether release continues for minutes, hours, days, weeks, months or years, burst can be considered to occur during minutes (or even less), hours, weeks or even up to a few weeks. Release in the context of this invention is typically considered burst release if the release of the burst is 10% or more of the total release within a time period of 3% or less, preferably 1% or less, of the time period of the total release. In the embodiments exemplified in this application burst occurs within the first 30 to 60 minutes.

Encapsulated agents should be understood to be drugs, active pharmaceutical ingredients (API) and other functional, therapeutic and biologically active agents that are inside of the sol-gel derived silica materials.

Biologically active agent in the context of this invention refers to any organic or inorganic agent that is biologically active, i.e. it induces a statistically significant biological response in a living tissue, organ or organism. The biologically active agent can be a medicine, peptide, polysaccharide or a polynucleotide, e.g. DNA and RNA. It can be an agent for treatment of diseases in therapeutic areas like alimentary/metabolic, blood and clotting, cardiovascular, dermatological, genitourinary, hormonal, immunological, infection, cancer, musculoskeletal, neurological, parasitic, ophthalmic, respiratory and sensory. It can further be for treatment of diseases like osteoporosis, epilepsy, Parkinson's disease, pain and cognitive dysfunction. It can be an agent for the treatment of hormonal dysfunction diseases or hormonal treatment e.g. for contraception, hormonal replacement therapy or treatment with steroidal hormones. It can further be an agent such as an antibiotic or antiviral, anti-inflammatory, neuroprotective, prophylactic vaccine, memory enhancer, analgesic (or analgesic combination), immunosuppressant, antidiabetic or an antiviral. It can be an antiasthmatic, anticonvulsant, antidepressant, antidiabetic, or antineoplastic. It can be an antipsychotic, antispasmodic, anticholinergic, sympathomimetic, antiarrhythmic, antihypertensive, or diuretics. It can be an agent for pain relief or sedation. It can also be a tranquilliser or a drug for cognitive dysfunction. The agent can be in a free acid or base form, a salt or a neutral compound. It can be a peptide, e.g. levodopa; or an antibody fragment. It can be a polynucleotide, a soluble ion or a salt.

In the context of this invention the term active pharmaceutical ingredient, API, refers to any substance or mixture of substances intended to be used in the manufacture of a drug (medicinal) product and that, when used in the production of a drug, becomes an active ingredient of the drug product. Such substances are intended to furnish pharmacological activity or other direct effect in the diagnosis, cure, mitigation, treatment, or prevention of disease or to affect the structure or function of the body.

In the context of this invention solid content refers to the proportion of non-volatile material contained in a suspension left after the volatile solvent has vaporized. More particularly it can refer to the solid content of the silica sol used to obtain the hydrogel composition of the invention or the solid content of the silica hydrogel composition of the invention.

When referring, in the context of the present invention, to that the hydrogel composite comprises a particular weight percent (wt-%) of silica particles, then the wt-% is calculated from the amount of silica particles and silica sol used to obtain the hydrogel composite. Thus, if e.g. 100 g of silica particles is mixed with 900 g of silica sol, then the wt-% of silica particles in the hydrogel composition is 10 wt-%. If the silica hydrogel is obtained by first preparing a suspension of the silica particles then the percentage is calculated from the original weight of the silica particles in comparison to final weight (then being the weight of the silica particles+the weight of liquid used to make a suspension of the silica particles+the weight of the silica sol) of the silica hydrogel composition.

Features of the Invention

The present invention, an all-silica microparticle-hydrogel composite with high microparticle concentration is illustrated by comparing its main features to different materials, e.g., to the properties of the separate components of the invention, such as gels and microparticles and to other gel and hydrogel systems. Gels as drug delivery systems are often preferred, because they are soft and they can usually be injected into a target tissue in the form of a sol or a macromolecular solution before they turn into a gel. However, they usually have a loose structure, which may results in a burst (the general principle is illustrated in FIG. 1) and also in diffusion-controlled release especially with small-molecule drugs. The microparticles in turn can be easily combined with water and other liquids to form injectable suspensions, but due to relatively fast drying during a typical microparticle preparation process, i.e. spray-drying, a large amount of a drug may be located near the outer surface (especially in high drug loading), which causes the burst release.

The present invention provides a composite formulation consisting of separate components, in which the release is mainly controlled by matrix (silica microparticle) biodegradation rate and the burst is remarkably decreased compared with conventional controlled release systems. The preferable type of the composite formulations is a composite of different silica morphologies that together in an integrated structure have unique controlled release properties compared with the same silica morphologies as such. Also other substances, such as polysaccharide-based materials combined with different silica or polysaccharide morphologies result in materials with unique controlled release properties compared with the materials as such. One of the features of the present inventions is that the combined compositions are easy to handle and it is easy to mix the separate components into a homogeneous, injectable formulation.

In the present invention the typical components of the composite formulation are: small particles, nanoparticles or microparticles, preferably silica-based microparticles prepared by, e.g., spray-drying; and sols and/or solutions (e.g., silica sols). After combination of the components, or after combination of the components and application into tissue or tissue fluids or to simulated body/tissue fluids (or corresponding), an integrated structure is formed that can be defined to be a gel, a hydrogel or an organogel, preferably a hydrogel. The gel is preferably a silica-based hydrogel, but can also be a polysaccharide-based hydrogel, e.g., a chitosan-based hydrogel or a gel, where both the liquid and solid phase of the gel may consist of several substances. In the present invention a typical gel consists of a continuous solid phase with liquid homogeneously dispersed within the solid phase and where the elastic modulus of the material is higher than viscous modulus indicating that the solid phase dominates the properties of the composite formulation.

One of the important properties of the combined compositions is that they are injectable, e.g., with thin needles such as 18-25 G (the outer diameter of 25 G is 0.5 mm, the inner diameter varies, it is commonly ≤0.24 mm; the outer diameter of 18 G is 1.27 mm, the inner diameter varies, it is commonly ≤0.84 mm) or they are applied trough a catheter or hoses/tubings in which the shear stress is lower and even the particle size can be larger, but preferably below 2 mm. The combined compositions, i.e. the composites of the invention, are injectable, flowing and/or extrudable, because they are shear-thinning. Thus the viscosity of the composite of the invention is substantially decreased due to shear stress during injection or the like and after injection or the like, when the composite is no more exposed to shear stress, the original viscosity of the gel is restored. Thus, one feature of the combined compositions of gels and particles is inject-ability of the composite of the invention, compared with the injectability of a gel or a microparticle suspension. The addition of particles, such as microparticles into a gel may act as a ball bearing and make the injection easier with high particle concentrations, such as >50 wt-% or the addition of a gel may make the injection of a microparticle suspension easier by changing the overall rheological properties.

In the present invention, a certain amount of particles, preferably 50-85 wt-% of the total combined formulation and preferably having a particle size distribution less than 150 µm are combined with a sol and/or a solution having typically a low dry content, such as 1-5 wt-0% of silica or other material. The microparticles contain typically 3-45 wt-% of encapsulated agents (even higher concentrations are possible), such as drug(s)/active pharmaceutical ingredients (API) or other therapeutic or biologically active agents. After the combination of the microparticles and/or a sol/solution a flowing and injectable integrated structure is first formed after which the integrated structure turns into a gel composite structure (a sol-gel transfer) within a time that can be controlled by the formulation recipe or by selecting a time point at which the composite is injected into tissue, tissue/body fluid or to simulated body/physiological/tissue fluids or corresponding. Some of the flowing composite formulations, e.g., silica microparticle-silica sol based formulations turn into gels spontaneously after the combination within a time that can be adjusted with the recipe and/or storage temperature. Some of the flowing composite formulations may turn into gel after they are injected into tissue, tissue fluid or corresponding. However, independently on the method to form the (hydro)gel the resulting composite structure has unique controlled delivery properties, especially with respect to the control of the burst. In the present invention the burst is illustrated by measuring the amount of the encapsulated agent released (in/into tissue, tissue/body fluids, and/or simulated body/physiological/tissue fluids) in the beginning of the release and typically within the first 30-60 minutes. E.g., a burst of 30% can mean that 30% of the total amount of the encapsulated agent is released within 30-60 minutes.

The properties of the composite formulations are surprising because already a small amount of a sol or a solution with a low dry content changes the properties of the controlled release system clearly when combined with microparticles [e.g., 2 wt-% of silica or chitosan in water is combined with silica microparticles typically in weight ratios (sol/solution-to-microparticles) from 10:90 to 50:50]. The addition of a sol/solution increases the total dry content of the composite gel structure only a little, but the resulting structure is totally different compared with the microparticles or gels as such and the influence on the controlled release of encapsulated agents is remarkable. Especially the burst of the encapsulated agents is remarkably decreased compared with the burst from the microparticles or the gels as such.

In typical examples of the present invention the burst of a hydrophilic, highly water-soluble model molecule from composite formulations (a hydrogel formed from a silica sol or other sols/solutions and silica microparticles with the encapsulate model molecule) decreased 2-4 times compared with the microparticles or gels as such. For a hydrophobic drug molecule the observed decrease in the burst from the corresponding composite formulations was even higher being typically 5-20 times lower from the composite formulation compared with the microparticles or gels as such (e.g., a burst of 30% from the silica microparticles as such, but only 3% from the hydrogel composite formulation prepared from the same silica microparticles and a silica sol or a chitosan sol/solution). The examples of the present invention show that the clear decrease in the burst is observed, when the combined structure of microparticles and a sol/solution turns into a hydrogel. However, when the corresponding silica microparticles are combined with a solution that form an organogel (a gel where the liquid phase is not water, but some organic liquid and also the solid phase is typically consisting of organic substance(s)), such as Sorbitan monostearate-based organogels, no decrease in the burst is observed. Thus, the water phase in the resulting gel structure is of importance and there are several possibilities why it has an influence on the burst. In addition to the water phase in the hydrogel structure, the viscoelastic properties of the gels have an influence on the burst.

The hydrogels, as any gels in general are structures where the solid phase is the continuous phase and the liquid phase is homogeneously dispersed in the solid phase and the structure can be characterized to be non-flowing. The concept of "hydrogel" is commonly used when the liquid phase is water or a water-based solution. For any gel, the elastic properties (indicated by G', elastic/storage modulus) dominate over viscous properties (indicated by rheological methods by G", viscous/loss modulus) that can be measured by oscillation measurements with a rheometer with, e.g., a cone-plate geometry within the linear viscoelastic region under small angle oscillatory shear. If silica microparticles are combined with a sol and the combination of the silica microparticles and the sol does not turn into a hydrogel, but form a viscous, flowing mixture (indicated by e.g., that G', viscous/loss modulus dominates over the G" (elastic/storage) modulus over a range of different frequencies at different constant strains), no significant effect on the burst is observed and the release results correspond to those of plain silica microparticles. When comparing different hydrogels and their properties to each other, there is also some correlation between the magnitude of the elastic modulus and the decrease in the burst meaning that the hydrogels with higher elastic modulus seem to decrease the burst a bit more than hydrogels with lower elastic modulus. However, a clear effect is observed already for hydrogel structures with low elastic moduli that decrease the burst remarkably.

The great difference in the burst results between the hydrogels and the organogels and clear decrease in the burst already for the hydrogels with low elastic modulus could suggest an integrated structure formed with help of the presence of water in the pores of the gels and/or local saturation of silica's dissolution product, silicic acid, in the pores of the hydrogel. In the present invention, the remarkable decrease in the burst is observed for composite formulations that all contain silica microparticles, but the formulation of the other component, a sol or a solution, may vary both with respect to the chemical substances and amount of different substances. The same remarkable decrease in the burst is observed both for silica- and chitosan-based composite hydrogels. Silica has a low solubility in water and, e.g., in amorphous form, such as silica microparticles of the present invention, it is ca. 130-150 ppm at neutral pH at room temperature. Although the solubility is low, the dissolution rate is commonly fast meaning that a local saturation (with respect to silica) in the liquid phase of both silica- and chitosan-based hydrogels in most likely to occur fast, most likely within minutes, at latest within hours. This is supported by the typical high total concentration of silica in the composite hydrogel structure, ca. 50-90 wt-% and mostly in the form of the silica microparticles both in the both silica- and chitosan-based hydrogels. If the local saturation occurs, it means that the silica microparticles that contain the encapsulated API molecule or corresponding dissolve only as the dissolution liquid is slowly changed by diffusion. It means that the silica microparticles dissolve slowly (much more slowly compared with the situation where silica microparticles are as such in dissolution medium) and hence, biodegradation-related release of the encapsulated API is also very slow. It is likely that the local saturation is not the only reason, because the release after the burst is commonly of the same order as for the plain silica microparticles. Some variation can be observed also in the general release results, but the clearest differences are observed in the burst in the beginning of the release.

In addition to the local saturation, it is likely that the presence of water support some kind of integration between the silica microparticles. Also the silica or chitosan present in the sol/solution may interact with the microparticles and act partly as "a glue" between the silica microparticles. In the silica sol-silica microparticles-based hydrogel structure it is also possible that both the presence of the nanoparcticles in the sols and saturated amount of silicic acid in the pores enhance the condensation between the silica microparticle surface and by that way the silica microparticle structure becomes "sintered" into a more integrated structure. As the integrated structure is formed, and it is actually indicated by the rheological measurements, it is likely that the effects due to the integrated structures are at strongest in the beginning of the dissolution in a release medium or corresponding. It is also obvious that an integrated structure forms a structure, where the average diffusion path becomes longer. The longer diffusion path has an influence both on the dissolution (biodegradation) of the matrix (common in bulk-eroding systems, such as silica gels) and the release of the encapsulated agents. When the dissolution of silica proceeds, the effect of the integrated structure becomes weaker with respect to the controlled release. It is, however, typical that the three-dimensional, gel-like structure is preserved for a long time after the burst. It is believed that when the composite hydrogel is placed into a release medium or tissue, the components originating from the sols (e.g., silica sol) degrade/dissolve/disintegrate faster than the silica microparticles. If a sintered-like structure is formed in a silica sol-silica microparticle-based hydrogel, it is likely that the newly formed integrating structures between the silica microparticles dissolve faster that silica microparticles itself. The amount of the components in the sols is also low compared with the silica microparticles. Hence, the influence of the composite structure is believed to be strongest in the beginning of the release and burst is remarkably decreased. The same phenomenon is possible also for other material combinations, such as composite hydrogels formed from chitosan microparticles and chitosan solution/sol as long as the soluble chitosan or chitosan nanoparticles interact so that they form an integrated structure that can be characterized to be a hydrogel, e.g., with help of rheological measurements.

The release results, however, observed for the combined hydrogel compositions formed from silica microparticles and chitosan sols/solutions are different. In that case both the burst and the overall release rate are remarkably slowed down, which indicate that the mechanism is different and the chitosan structure as such affects remarkably the release results.

The R-values in the sol formulations refer to molar water-to-TEOS ratio, e.g., R150 indicating that there is 150 mol of water per 1 mol of TEOS. The double R-value, e.g., R5-35 means that the initial molar water-to-TEOS ratio is 5, but after the hydrolysis the system is diluted with water (or with some other liquid, such as ethanol) so that the final molar water-to-TEOS ratio (or the liquid-to-TEOS ratio corresponds to the water amount in R35, e.g., ethanol is added the volume as water would have been added to obtain R35 meaning that the ethanol addition results in the same dry content of silica in the total sol volume) used in the spray-drying is 35.

In examples of the present invention, the results of the rheological measurements describe the structures and properties of the sols and gels and the results support also the conclusions made on the burst and release results. Based on the rheological results, it can be said that when combining the silica microparticles and sols, the resulting combined structure has to be in the form of a hydrogel in order to obtain a clear decrease in the burst. Both silica- and chitosan-based sols formed a hydrogel structure when combined with the silica microparticles, but only all-silica structure, i.e., silica microparticles combined with silica sols affected the burst only. For the combined hydrogel structures, the burst decreased clearly compared to the plain silica microparticles. When the silica microparticles are combined with a silica sol so that a hydrogel is not formed, no effect on the burst is observed. In addition, an organogel was also tested and the burst was not affected at all. The resulting combined hydrogel structure of silica microparticle and the organogel did not affect the burst at all.

In prior art hydrogels have been combined with different particles, mostly organic polymer particles with different organic gels, but also silica microparticles have been combined with organic materials to adjust the release kinetics and burst of active pharmaceutical ingredients. To our knowledge, none of them have combined the same material in different morphologies; in particular no combinations of ceramic materials, such as silica microparticle-silica hydrogel combinations have been studied. When using the same material in different morphologies, such as silica microparticle combined with a silica hydrogel, the resulting material is more practical from the viewpoint of toxicology, product development, safety and function. If both the microparticles and the hydrogel contain same chemical substances and they are made of the same precursors, the number of chemical substances and impurities stays low, there is no need to study combination effects of different substances and there is a lower risk that any harmful effect would be detected when the material is used in clinical applications. If ceramic materials, such as silica and organic polymers are combined, the biodegradation mechanism becomes more complex or unpredictable, which increases risks, e.g., tissue irritation, in clinical use. Ceramic materials, such as silica, degrade in physiological conditions (in tissue, in tissue/body fluids or in simulated tissue/body fluids) only by dissolution in water. Enzymes are not able to degrade ceramic materials, but they participate in the biodegradation of organic polymers. In addition, the enzyme-based degradation occurs often randomly, i.e., the enzymes degrade the structure so that smaller or larger pieces of the material may come loose during implantation and cause, e.g., irritation and inflammation. Hence, a ceramic-ceramic combination, such as silica microparticles-silica hydrogel degrades in a more predictable way and because enzymes are not able to degrade them, it is also probable that no sudden faster release of e.g. API caused by the sudden change in the structure (that could occur after a long implantation period) will occur for ceramic systems, but it may occur for any controlled release system based on the organic polymers/materials. Hence, it is beneficial to keep the concentration of organic polymers low or to avoid them totally as in the silica microparticles-silica hydrogel combinations.

In addition, extraction studies needed in many toxicological studies are easier to plan for ceramic delivery systems, e.g., all-silica composite structure, than for a ceramic-polymer composite. The liquids used in extraction are commonly designed so that both polar (e.g. water) and non-polar liquids (e.g., vegetable oils) are used. If the material to be extracted is composed of 2 different types of substances, e.g., ceramics and polymers, it increases the risks that the extract does not contain all substances of interest (because the extraction times are different for the ceramic and polymeric parts of the materials), which may increase the risk for harmful effects later when applying the materials in vivo or in clinical applications.

The same chemistry may also have clearly technical benefits, e.g., based on good interaction with the different morphologies of the same material. If the interaction between the components of a composite is strong, as can be expected for, e.g., a silica-silica system, even a low concentration of silica in the sol that turns into silica hydrogel may have remarkable effects. Gels are dispersions of 2 different phases, where the solid matter is the continuous phase and the solid matter has a dominating role (with respect to the material properties). The liquid phase is the dispersed phase and in hydrogels the liquid phase is a water phase. The gels are typically formed when large, polymeric molecules or long aggregates of nanoparticles in a sol (suspension) or a solution start to overlap and form even larger clusters or aggregates (due to changing concentration, temperature etc.) that finally results in the structure where the solid matter dominates over the liquid and the material turns from a flowing sol/solution into a non-flowing form, a gel. Because of the polymeric nature and nanoscale dimensions of the solid matter, it is also typical that the solid content in the sol and in a resulting gel may be low, typically lower than 5 wt-%, sometimes much lower than 1 wt-%. When this fact is combined with the system where both components have the same chemistry, such as silica-silica composites, it can be expected that already low silica concentrations in the silica sol may result in interesting hydrogel structures with unique properties when combined with silica microparticles.

Silica-based hydrogels are not commonly as strong (e.g., stiff) as the corresponding organic hydrogels, because the polymeric structure of silica differs clearly from that of typical organic polymers. Pure silica-based systems do not actually form any molecular polymers at all, but oligomers that can be quite linear in the beginning, but when the oligomer size increases, they turn into a cyclic structure that "condensate" into a nanoscale particle that forms a separate solid phase in a liquid. This 2-phase system of small nanoscale particles in a liquid is typically called a sol. When several nanoparticles are formed, they start to aggregate to larger structures that correspond to polymeric structures. The interaction between the silica nanoparticles is based on the van der Waals forces or in extreme cases there might also be chemical bonds between the very small particles. In any case, the "monomer" of a silica system is a nanoparticle that is much larger than the monomers in the typical organic polymers and also the flexibility of the aggregates is different than that of organic polymer chains. Hence, as the diameter of the thread-like, "polymeric structures" of silica is larger and when the interaction forces are also weaker, even the resulting (hydro)gel is weaker and usually less stiff (observed typically in the elastic modulus of the gels) than corresponding (e.g., with the same weight-% of solid matter) organic hydrogels.

This combination of weaker general gel structure and stronger nature of interaction with the silica particles provide several unique properties. Due to the non-flowing silica hydrogel structure, the silica microparticles stay homogeneously in the composite mixture (better than in any viscous system). However, as the general silica hydrogel structure is relatively weak, the hydrogel is easy to turn into flowing form by introducing shear stress, e.g., by injecting the hydrogel through a thin needle with a syringe and the structure turns back into a non-flowing gel after the shear ends. From the viewpoint of good interaction between different silica components, even the low dry content of silica in the sol integrates the silica microparticles and the silica nanoaggregates into a one hydrogel structure that has a remarkable effect on the release of API in the silica microparticles. The integrated structure seems to decrease the burst remarkably, but after the burst the release proceeds as from the silica microparticles as such. This makes the design of the release system simple and no large studies on the combined effect of the silica microparticles and the hydrogel on the release is needed. The burst is decreased remarkably due to the combined silica microparticle-silica hydrogel structure, but the release is otherwise controlled by silica microparticles only.

We have earlier shown that spray-dried silica microparticles can be adjusted to have different biodegradation (dissolution) rates on a large scale (and thus also release rates) (M. Jokinen, R. Viitala, H. Jalonen, "Method for preparing adjustably bioresorbable sol-gel derived $SiO_2$", WO 2005/082781; R. Viitala, M. Jokinen, S. Tuusa, J. B. Rosenholm and H. Jalonen, Adjustably Biodegradable Sol-Gel Derived $SiO_2$ Matrices for Protein Release (Journal of Sol-Gel Science and Technology 36 (2005) p. 147-156); R. Viitala, M. Jokinen, S-L. Maunu, H. Jalonen, J. B. Rosenholm, Chemical Characterisation of Bioresorbable Sol-Gel Derived SiO2 Matrices Prepared at Protein-Compatible pH (Journal of Non-Crystalline Solids 351 (2005) p. 3225-3234); R. Viitala, M. Jokinen and J. B. Rosenholm, Mechanistic Studies on Release of Large and Small Molecules From Biodegradable SiO2 (International Journal of Pharmaceutics, 336 (2007) p. 382-390)). By adjusting the parameters (silica sol formulation and parameters of the spray-drying process) properly, it is possible to prepare a dense structure (indicated, e.g., by low specific surface area) with a fast dissolution rate or vice versa. In other words, it is possible to adjust the "chemical and physical structures" so that even small-molecule drugs can be delivered in a controlled manner and release rate can be adjusted to be very fast (from hours to days) or slow (from weeks to months). The only drawback of the silica microspheres is that sometimes the burst is observed. It occurs when a drug is concentrated near the outer surface of the silica microparticles, e.g., due to the a large amount of a drug and/or due to low solubility in the silica sol and/or due to large differences in the hydrophobicity and/or due to the fast drying process. When the spray-dried silica microspheres are combined with a silica sol, the burst can be decreased when the integrated silica microsphere-silica sol structure turns into a hydrogel.

If the particle size is small enough, even a mixture (suspension) of dry silica powder and water may turn into a hydrogel. In addition to the particle size, this depends on many parameters, such as the number of free OH groups on the silica particle surfaces, the pore structure and pore size of the particles, temperature, pH, hydrophobicity of the particles (the encapsulated drug may affect the hydrophobicity), dry content of silica in the suspension and time. The timescale is important, because when silica particles are in water, hydrolysis occurs always, but depending on the parameters above, it may take minutes or months and extensive hydrolysis is needed before the suspension may turn into a hydrogel. From the viewpoint of preparing a controlled release matrix for drug delivery the gelation occurring within a long time is not the best possible with respect to the homogeneity of the hydrogel with an encapsulated drug. A fast gelation ensures the homogeneous distribution of a drug also in those cases when the solubility of the drug in silica sol is low or when having larger biologically active agents. It is also typical that microscale silica particles (particle size ≥1 μm) do not form a gel when suspended with water. This is due to the non-colloidal size that is too large for a homogeneous 2-phase system and in some cases also due to the typical dense outer structure of the spray-dried silica microparticles. However, already a small amount of silica nanoparticles in the silica sol (described more in detail above) is enough to form a composite hydrogel that is potential in reducing the burst.

Hence, in the present invention, a new type of an injectable, all-silica-based silica microparticle-silica hydrogel controlled release system is introduced, which reduces the burst remarkably with different types of API and other therapeutic and biologically active agents.

PREFERRED EMBODIMENTS

In preferred silica hydrogel composites of the present invention the silica sol has a solid content of ≤3 wt-% and preferably ≤1 wt-%.

Typically the that the silica particles employed for preparing the silica hydrogel composite of the present invention comprise from 0.1 to 70 wt-%, preferably from 0.3 to 50 wt-%, and most preferably from 1 to 30 wt-% of the encapsulated agent. More precisely the composite typically comprises ≥0.1 wt-%, preferably ≥0.3 wt-%, more preferably ≥1 wt-%, even more preferably ≥3 wt-% and most preferably ≥5 wt-%; and/or typically ≤70 wt-%, preferably ≤60 wt-%, more preferably ≤50 wt-%, even more preferably ≤45 wt-% and most preferably ≤30 wt-%.

The silica particles employed for preparing the silica hydrogel composite of the present invention are microparticles typically having a diameter between 1 μm and 300 μm, preferably 1 μm and 100 μm, more preferably 1 μm and 30 μm and most preferably 1 μm and 20 μm.

The silica particles employed for preparing the silica hydrogel composite of the present invention are particles typically having a diameter between 50 nm and 1 000 nm, preferably between 100 nm and 1 000 nm, most preferably between 200 nm and 1 000 nm.

The silica hydrogel composite of the present invention typically comprises from up to 80 wt-%, preferably 30 to 80 wt-%, most preferably 50 to 80 wt-% of the silica particles.

The present inventions silica hydrogel composite solid content is typically from 20 wt-% to 70 wt-%, preferably from 30 wt-% to 60 wt-% and most preferably from 40 wt-% to 55 wt-%. More precisely the solid content is typically ≥20 wt-%, preferably 30 wt-% and most preferably ≥40 wt-%; and/or ≤75 wt-%, preferably ≤60 wt-% and most preferably ≤55 wt-%.

The elastic modulus of the silica hydrogel composite of the present invention measured under small angle oscillatory shear in the linear viscoelastic region is <300 kPa, preferably <100 kPa and most preferably <30 kPa.

In some embodiments of the invention the encapsulated agent is fluorescein.

The encapsulated agent of the silica hydrogel composite of the present invention typically is a biologically active agent. Preferably the biologically active agent is an active pharmaceutical ingredient, API, such as nimodipine.

Typically the water solubility of the encapsulated agent of the silica hydrogel composite of the present invention is ≤10 mg/ml, more preferably ≤3 mg/ml, even more preferably ≤1 mg/ml, even more preferably ≤0.3 mg/ml, still more preferably ≤0.1 mg/ml and most preferably ≤0.03 mg/ml.

Typically the molecular weight of the encapsulated agent of the silica hydrogel composite of the invention is ≤10 000, preferably ≤3 000, more preferably ≤1 000, most preferably from 100 to 500.

Preferably the silica particles are selected from the group consisting of spray dried silica particles, silica fibre fragments and moulded or casted silica monoliths as such or as crushed.

Typically use of the silica hydrogel composite of the invention is for an injectable formulation injectable through a needle, preferably with an inner diameter of ≤10 mm, more preferably ≤3 mm, even more preferably ≤1 mm and most preferably ≤0.3 mm; or for a flowing formulation for a catheter or tubing with an inner diameter of ≤30 mm, preferably ≤10 mm, more preferably ≤3 mm, even more preferably ≤1 mm, and most preferably ≤0.3 mm.

The typical medical use of the silica hydrogel composite of the invention is for parenteral administration or surgical implantation. Preferably parental administration is selected from the group consisting of intravenous, intraarterial, intracardiac, topical, transdermal, intradermal, subcutaneous, intramuscular, intraperitoneal, intracerebral, intracerebroventricular, intrathecal, intraosseous, intraarticular, intraocular, intrasternal, intravesical and intracavernosal.

In a preferred method of the present invention the silica sol has a solid content of ≤3 wt-% and most preferably ≤1 wt-%.

The silica particles employed in the method of the present invention typically comprise from 0.1 to 70 wt-%, preferably from 0.3 to 50 wt-%, and most preferably from 1 to 30 wt-% of the encapsulated agent. More precisely the silica particles typically comprise ≥0.1 wt-%, preferably ≥0.3 wt-%, more preferably ≥1 wt-%, even more preferably ≥3 wt-% and most preferably ≤5 wt-%; and/or typically ≤70 wt-%, preferably ≥60 wt-%, more preferably ≤50 wt-%, even more preferably ≤45 wt-% and most preferably ≥30 wt-%.

In some embodiments the silica particles employed in the method of the present invention are microparticles having a diameter between 1 μm and 300 μm, preferably between 1 μm and 100 μm, more preferably between 1 μm and 30 μm and most preferably between 1 μm and 20 μm.

In other embodiments the silica particles employed in the method of the present invention are particles having a diameter between 50 nm and 1 000 nm, preferably between 100 and 1 000 nm and most preferably between 200 nm and 1 000 nm.

Typical methods of the present invention result in hydrogel composites comprising from up to 80 wt-%, preferably 30 to 80 wt-%, most preferably 50 to 80 wt-% of the silica particles.

Typical methods of the present invention result in hydrogel composites with a solid content from 20 wt-% to 75 wt-%, preferably from 30 wt-% to 60 wt-% and most preferably from 40 wt-% to 55 wt-%. More precisely the solid content is typically ≥20 wt-%, preferably ≥30 wt-% and most preferably ≥40 wt-%; and/or ≤70 wt-%, preferably ≤60 wt-% and most preferably ≤55 wt-%.

Typically the silica particles employed in the method of the present invention are prepared by a sol-gel process. Preferably the silica particles are selected from the group consisting of spray dried silica particles, silica fibre fragments and moulded or casted silica monoliths as such or as crushed.

FIGURES

FIG. 1 illustrates burst release.

Figure 2:
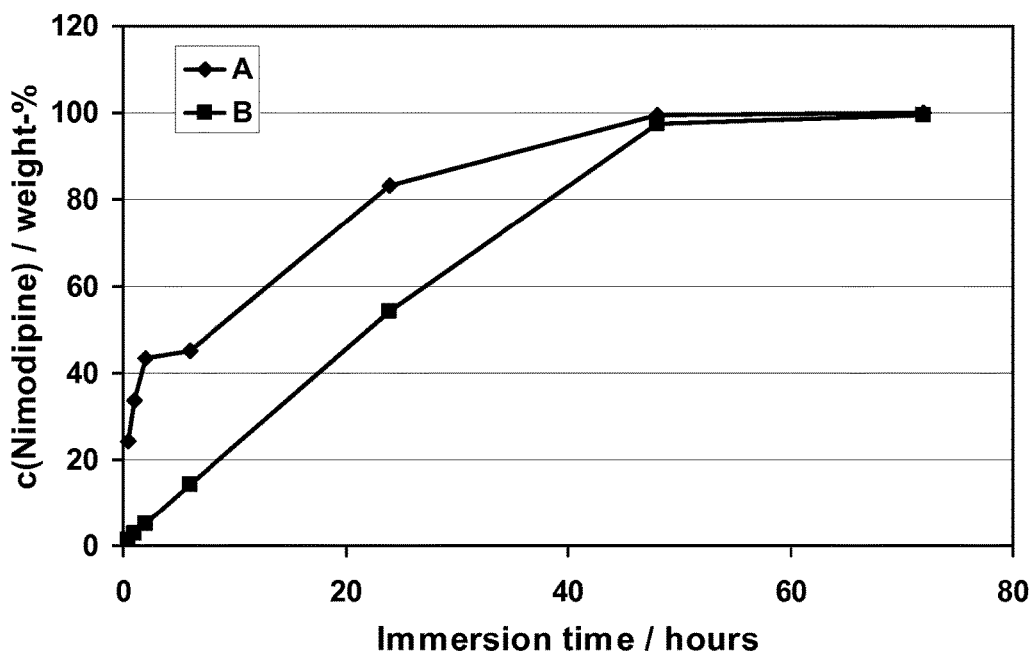
FIGS. 2-9 illustrate the release rates of nimodipine from different gels, silica microparticles and combined composition.

FIG. 2 illustrates cumulative release of nimodipine from R6-50 MP silica microparticles with 15% (w/w) loading of nimodipine (A) and from the combined hydrogel composition of R6-50 MP+R100 with 15% (w/w) loading of nimodipine in R6-50 MP (B).

Figure 3:
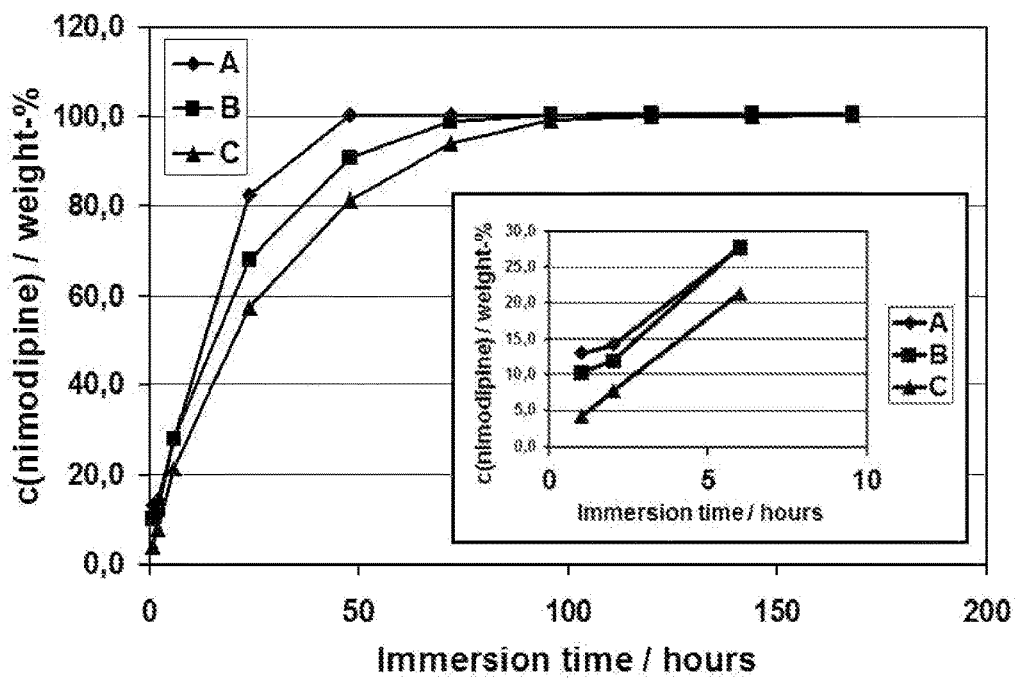

FIG. 3 illustrates cumulative release of nimodipine from R150 gel (45 mg/ml nimodipine) (A), R5-35 MP with 6% (w/w) loading of nimodipine (B) and combined hydrogel composition formed from R5-35 (MP) silica microparticles+R150 silica sol with 6% (w/w) loading of nimodipine in R5-35 (MP) silica microparticles (C). The first 6 hours of the release is shown separately in the zoomed graph. The zoomed graph indicates the differences in the burst (here the released amount at 60 minutes).

Figure 4:
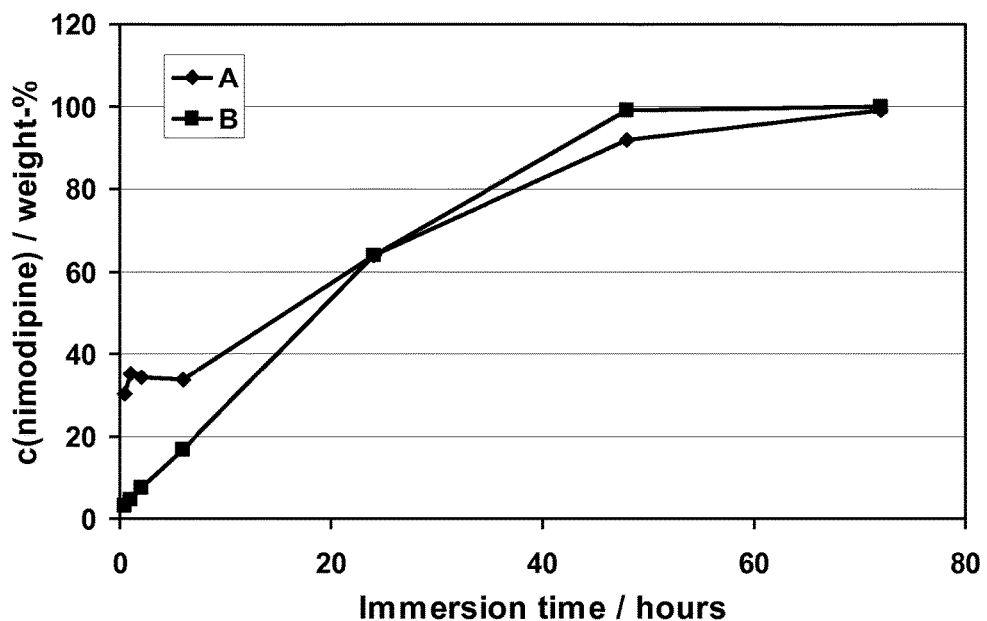

FIG. 4 illustrates cumulative release of nimodipine from R4-50 MP silica microparticles with 30% (w/w) loading of nimodipine (A) and from the combined hydrogel composition formed from R4-50 MP silica microspheres+R150 silica sol with 30% (w/w) loading of nimodipine in R4-50 MP (B).

Figure 5:
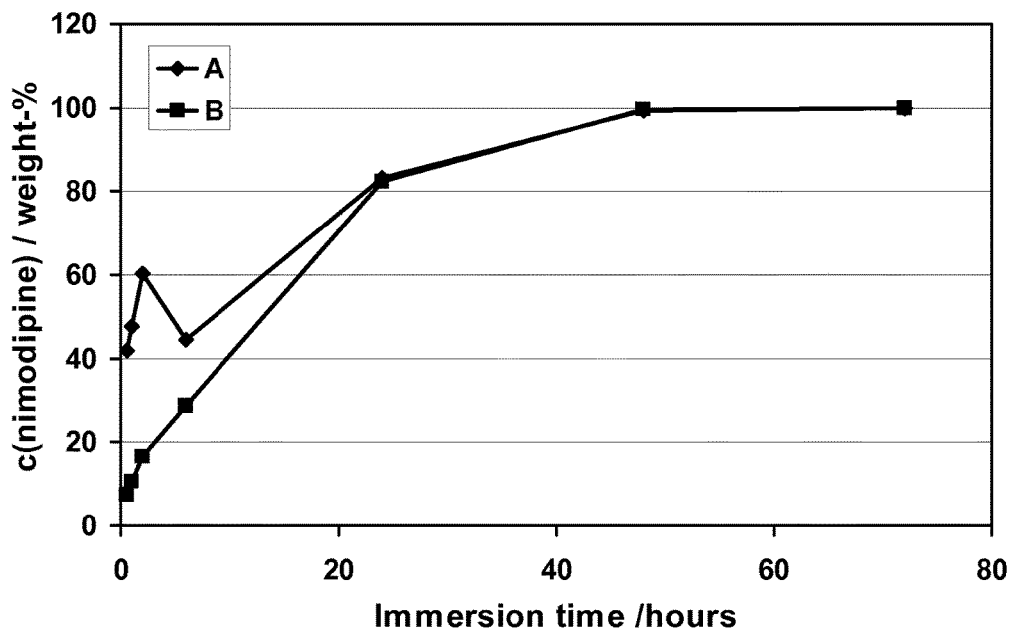

FIG. 5 illustrates cumulative release of nimodipine from R5-50 MP silica microparticles with 15% (w/w) loading of nimodipine (A) and from the combined hydrogel composition formed from R5-50 MP silica microparticles+R300 silica sol with 15% (w/w) loading of nimodipine in R5-50 MP (B).

Figure 6:
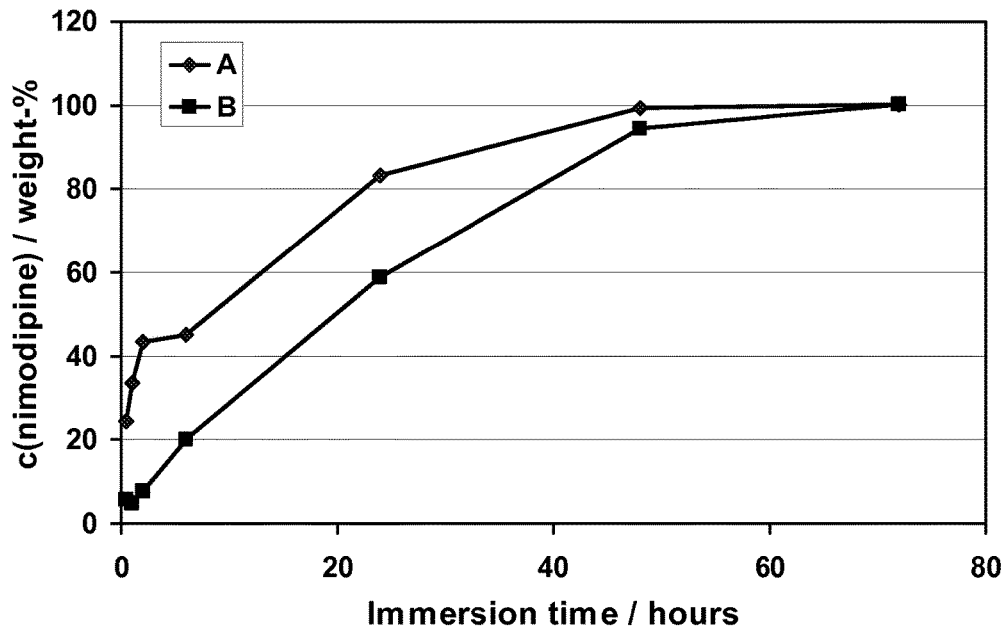

FIG. 6 illustrates cumulative release of nimodipine from R6-50 MP silica microparticles with 15% (w/w) loading of nimodipine (A) and from the combined hydrogel composition formed from R6-50 MP silica microparticles+R400 silica sol with 15% (w/w) loading of nimodipine in R6-50 MP (B).

Figure 7:
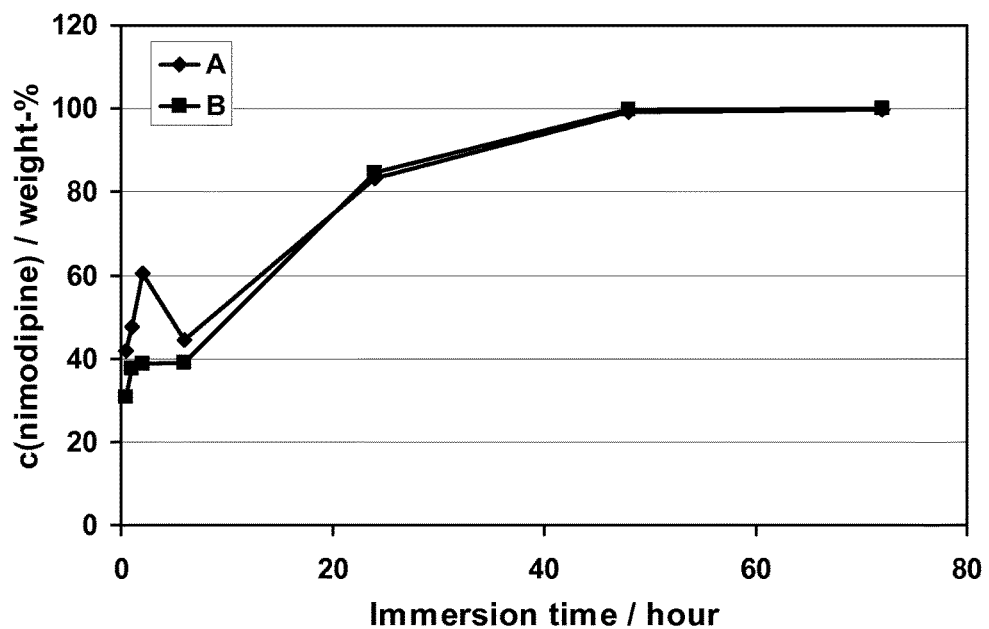

FIG. 7 illustrates cumulative release of nimodipine from R5-50 MP silica microparticles with 15% (w/w) loading of nimodipine (A) and from the combined hydrogel composition formed from R5-50 MP silica microparticles+R500 silica sol with 15% (w/w) loading of nimodipine in R5-50 MP (B).

Figure 8:
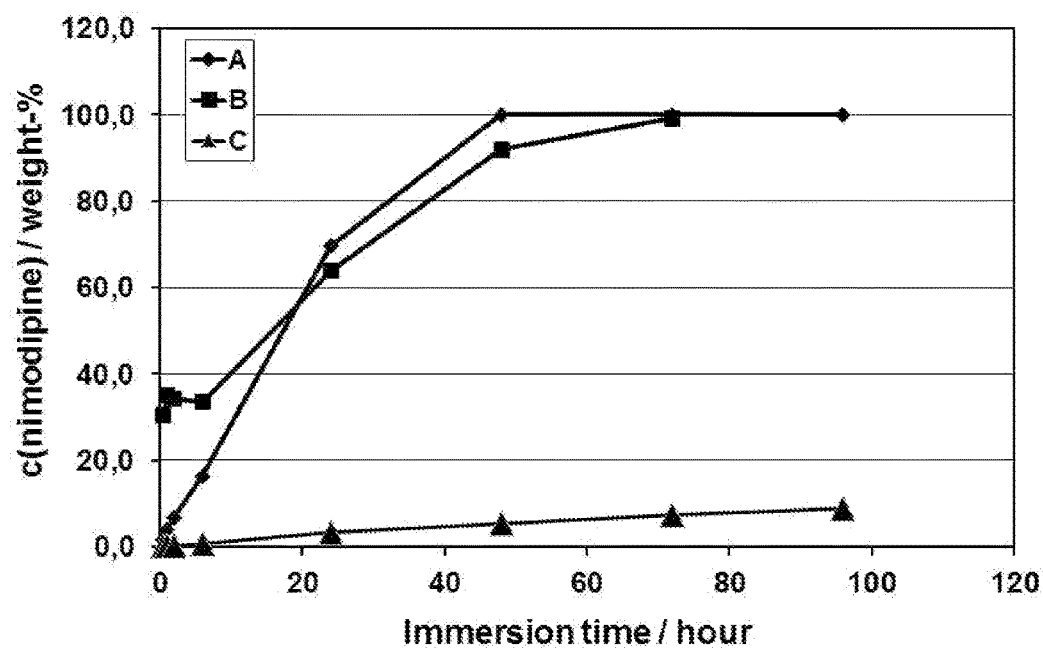

FIG. 8 illustrates cumulative release of nimodipine from 2% Chitosan gel (concentration of nimodipine 105 mg/ml chitosan sol/solution) (A), R4-50 MP silica microparticles with 30% (w/w) loading of nimodipine (B) and from the combined composition formed from R4-50 MP silica microparticles+2% Chitosan sol/solution with 30% (w/w) loading of nimodipine in R4-50 MP (C). The burst (released amount at 30 minutes is 0% for the combined hydrogel composition (0.1% at 60 minutes), 1.7% for chitosan gel and 30.3% for R4-50 MP.

Figure 9:
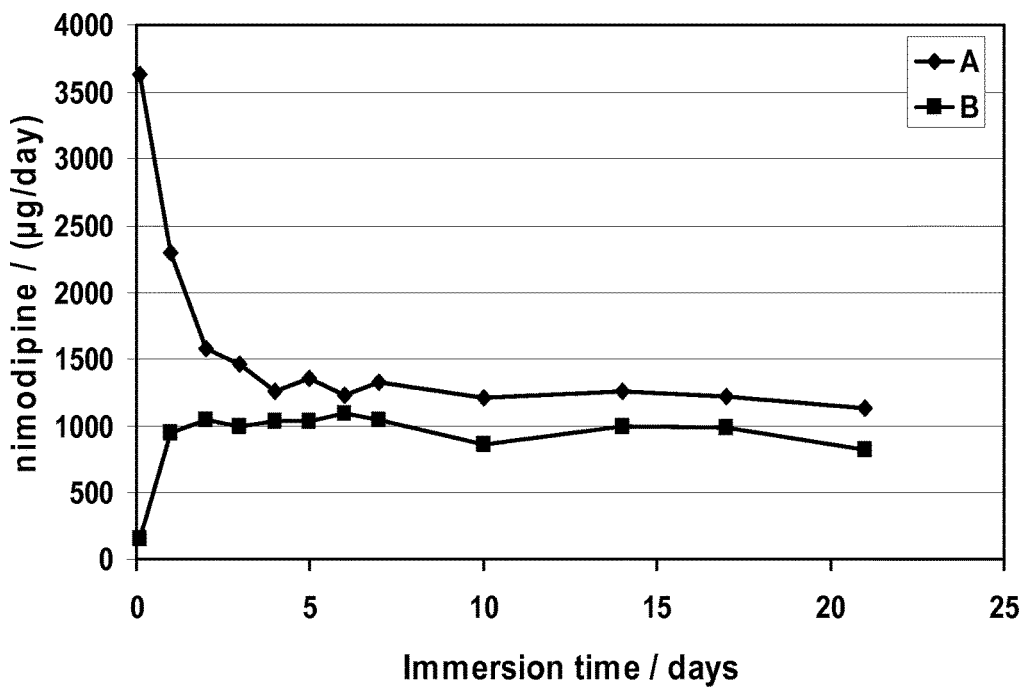

FIG. 9 illustrates release of nimodipine from R150 MP silica microparticles with 6% (w/w) loading of nimodipine (A) and from the combined hydrogel composition formed from R5-35 MP silica microparticles+R150 silica sol with 6% (w/w) loading of nimodipine in R5-35 MP (B) in a flow-through dissolution. Flow rate of the dissolution medium was 500 ml/day.

Figure 10:
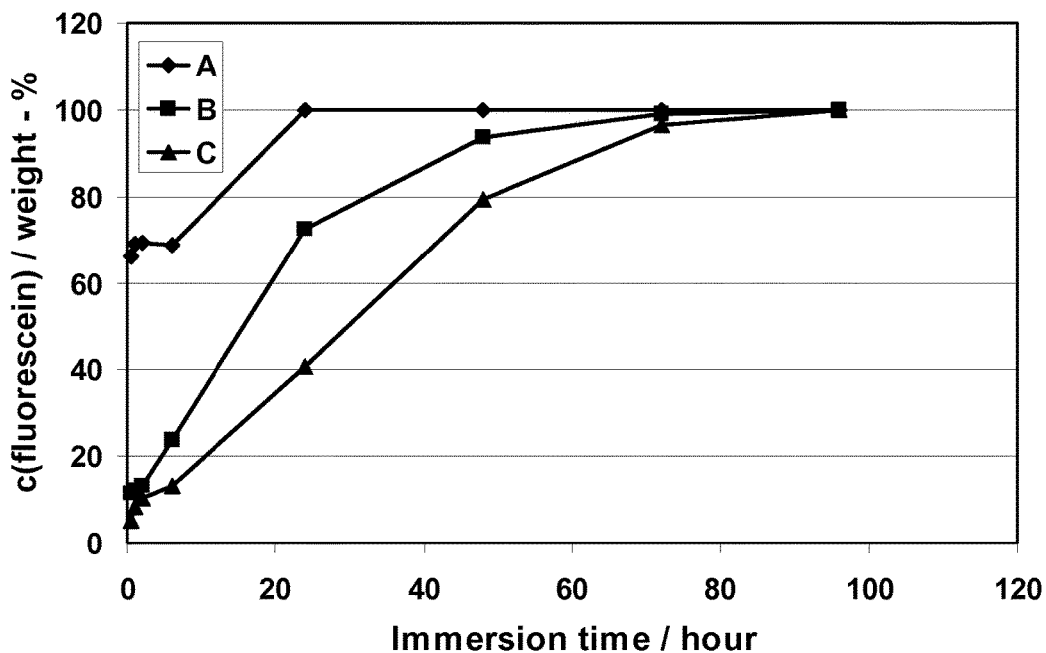
FIGS. 10-13 illustrate the release rates of fluorescein from different gels, silica microparticles and combined composition.

FIG. 10 illustrates cumulative release of fluorescein from R150 silica hydrogel (105 mg/ml fluorescein) (A), R5-50 MP silica microparticles with 15% (w/w) loading of fluorescein (B) and from the combined hydrogel composition formed from R5-50 MP silica microspheres+R150 silica sol with 15% (w/w) loading of fluorescein in R5-50 MP (C).

Figure 11:
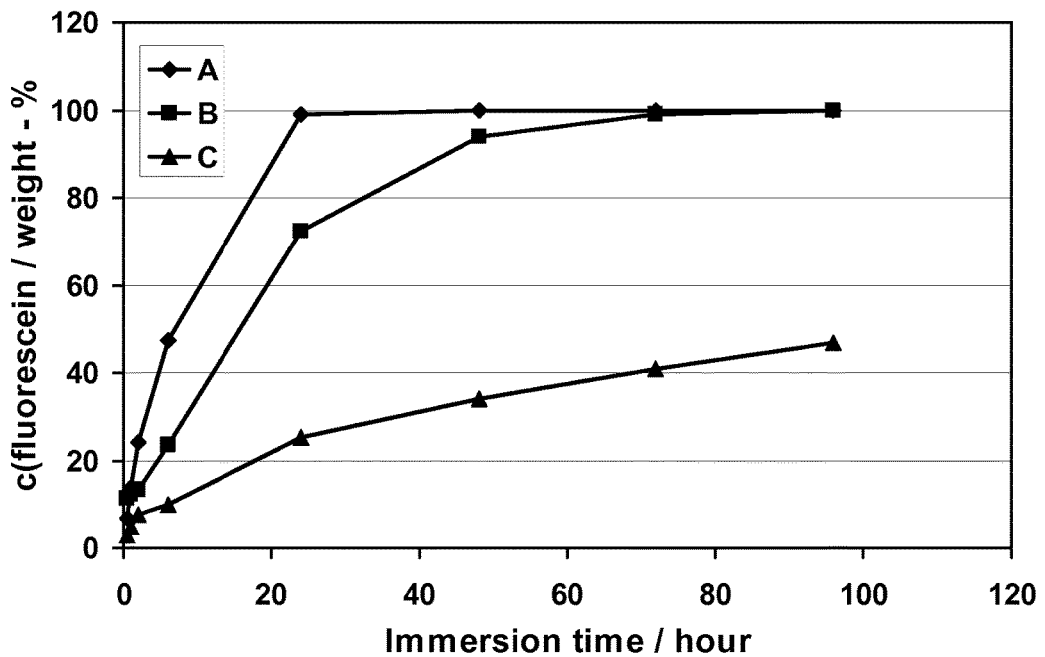

FIG. 11 illustrates cumulative release of fluorescein from 2% Chitosan gel (52.5 mg/ml fluorescein) (A), R5-50 MP silica microparticles with 15% (w/w) loading of fluorescein (B) and from the combined hydrogel composition formed from R5-50 MP silica microparticles+2% chitosan sol/solution with 15% (w/w) loading of fluorescein in R5-50 MP (C).

Figure 12:
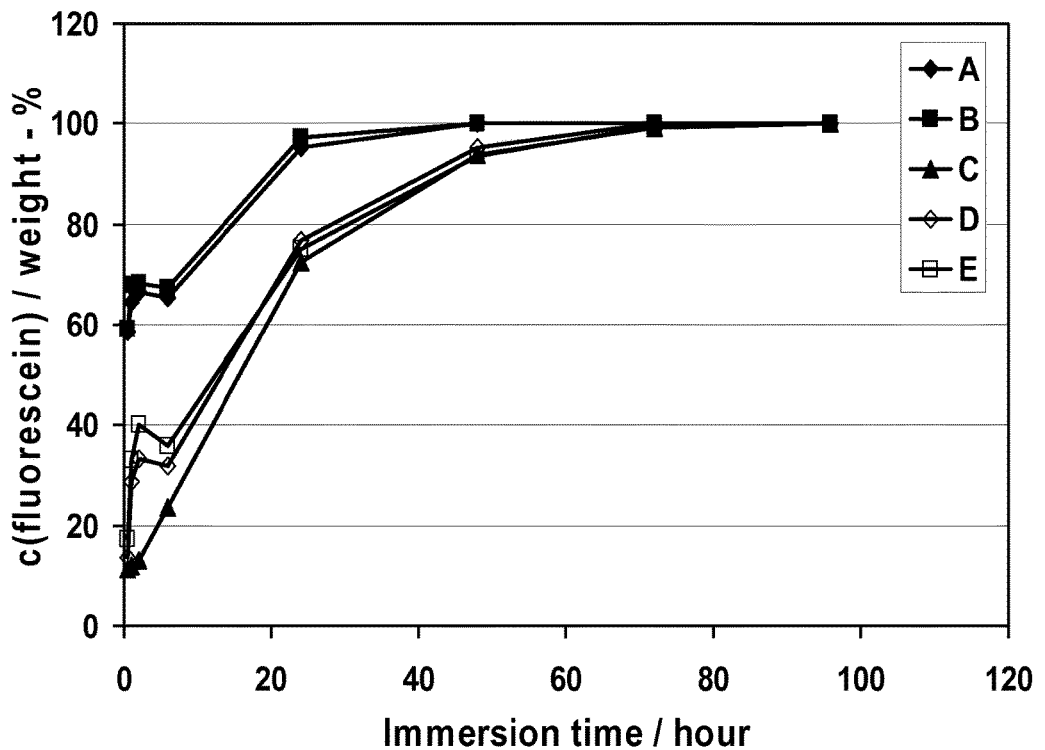

FIG. 12 illustrates cumulative release of fluorescein from 2% SMS gel (105 mg/ml fluorescein) (A), 15% SMS gel (105 mg/ml fluorescein) (B), R5-50 MP with 15% (w/w) loading of fluorescein (C), from the combined organogel composition formed from R5-50 MP silica microparticles+2% SMS with 15% (w/w) loading of fluorescein in R5-50 MP (D) and from the combined organogel formed from R5-50 MP silica microparticles+15% SMS with 15% (w/w) loading of fluorescein in R5-50 MP (E).

Figure 13:
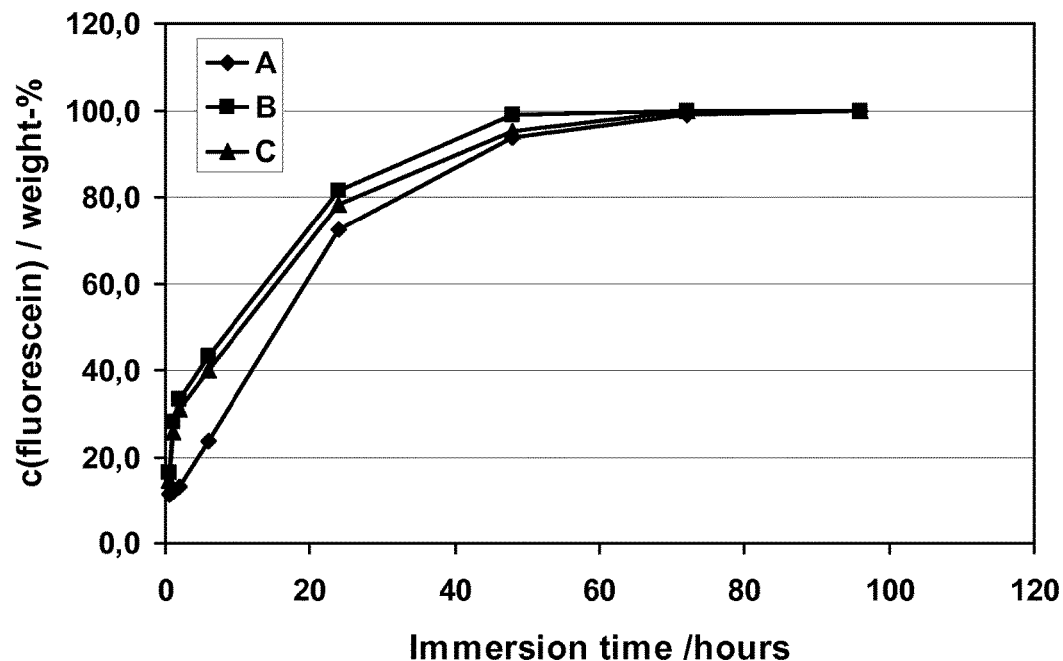

FIG. 13 illustrates cumulative release of fluorescein from silica microparticles R5-50 MP with 15% (w/w) loading of fluorescein (A), from the combined flowing composition of R15 silica sol+R5-50 MP with 15% (w/w) loading of fluorescein and with the silica microparticle concentration of 0.1 g/ml (B) and from the combined flowing composition of R15 silica sol+R5-50 MP with 15% (w/w) loading of fluorescein and with the silica microparticle concentration of 0.5 g/ml (C).

Figure 14:
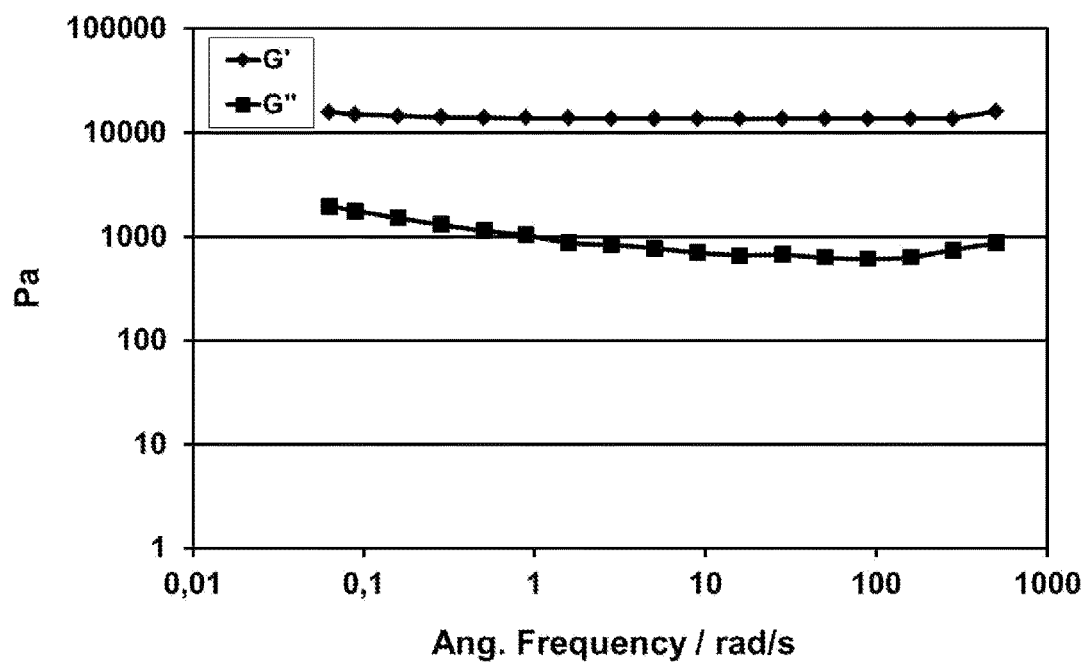
FIGS. 14-19 illustrate rheological properties, i.e., elastic (storage) modulus, viscous (loss) modulus and dynamic viscosity for different combined compositions.

FIG. 14 illustrates elastic (storage) modulus (G') and viscous (loss) modulus (G") for the combined hydrogel composition (aged for 1 day in a closed syringe that is stored in a closed aluminium foil at room temperature before the measurement) formed from silica microparticles R5-35 MP (with 6% (w/w) loading of nimodipine) and silica sol R150.

Figure 15:
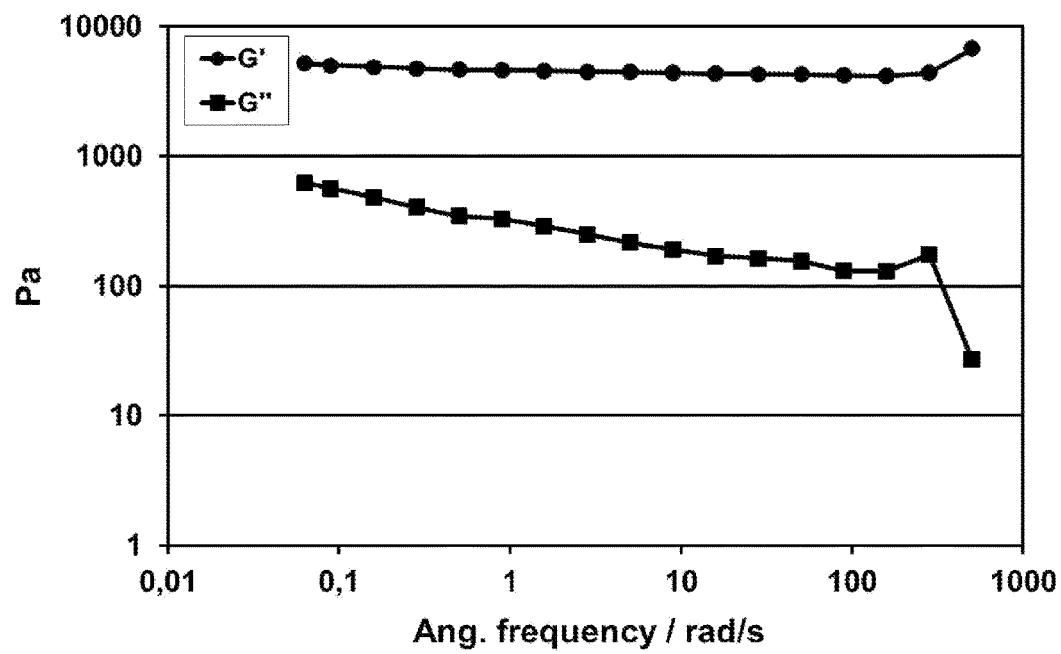

FIG. 15 illustrates elastic (storage) modulus (G') and viscous (loss) modulus (G") for the combined hydrogel composition (aged for 1 week at room temperature in a closed aluminium foil package) formed from silica microparticles R6-50 MP [with 15% (w/w) loading of nimodipine] and silica sol R400.

Figure 16:
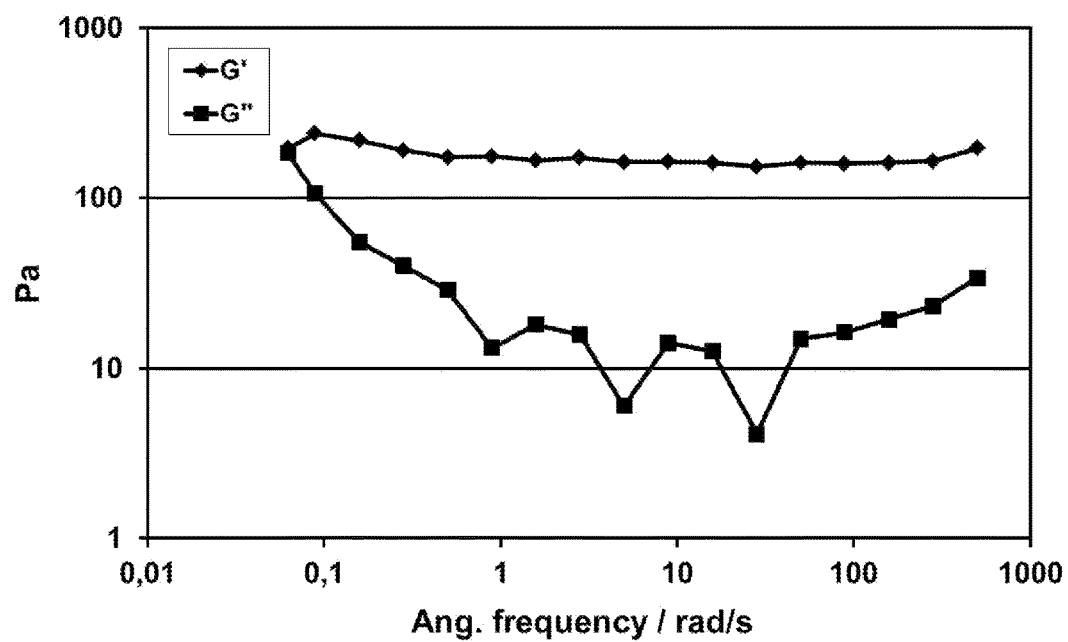

FIG. 16 illustrates elastic (storage) modulus (G') and viscous (loss) modulus (G") for the fresh (measured right after the combination of the silica sol and the silica microparticles as the combined composition has turned into a hydrogel, i.e. within 6 hours) combined hydrogel composition formed from silica microparticles R6-50 MP (with 15% (w/w) loading of nimodipine) and silica sol R400.

Figure 17:
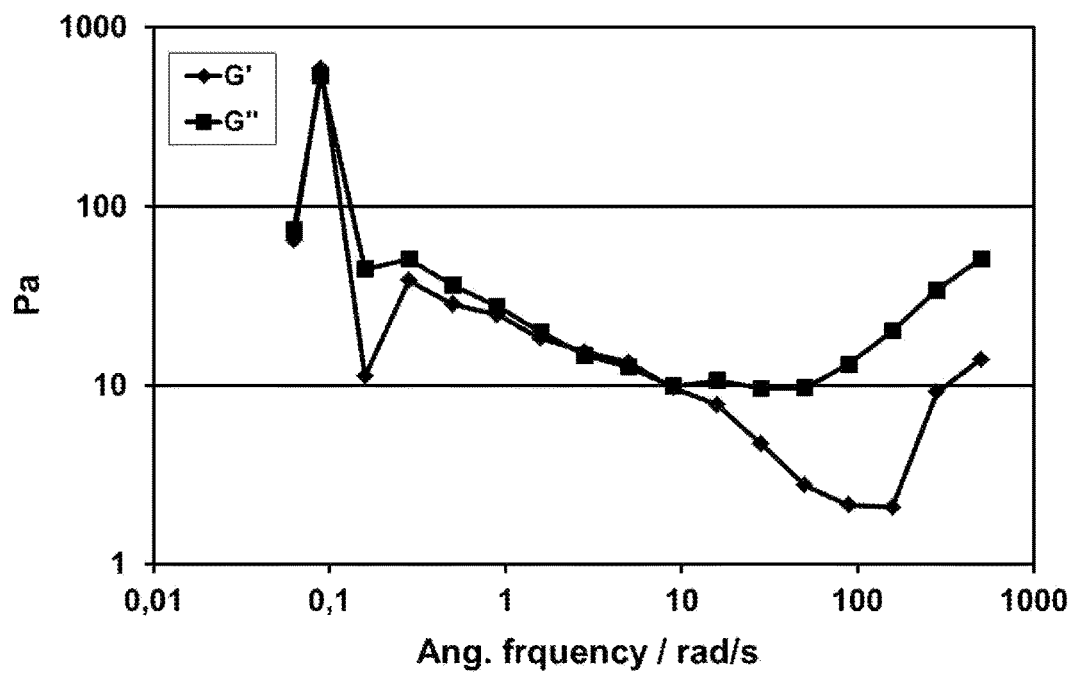

FIG. 17 illustrates elastic (storage) modulus (G') and viscous (loss) modulus (G") for the combined flowing composition of R15 silica sol+R5-50 MP with 15% (w/w) loading of fluorescein and with the silica microparticle concentration of 0.1 g/ml of R15 silica sol.

Figure 18:
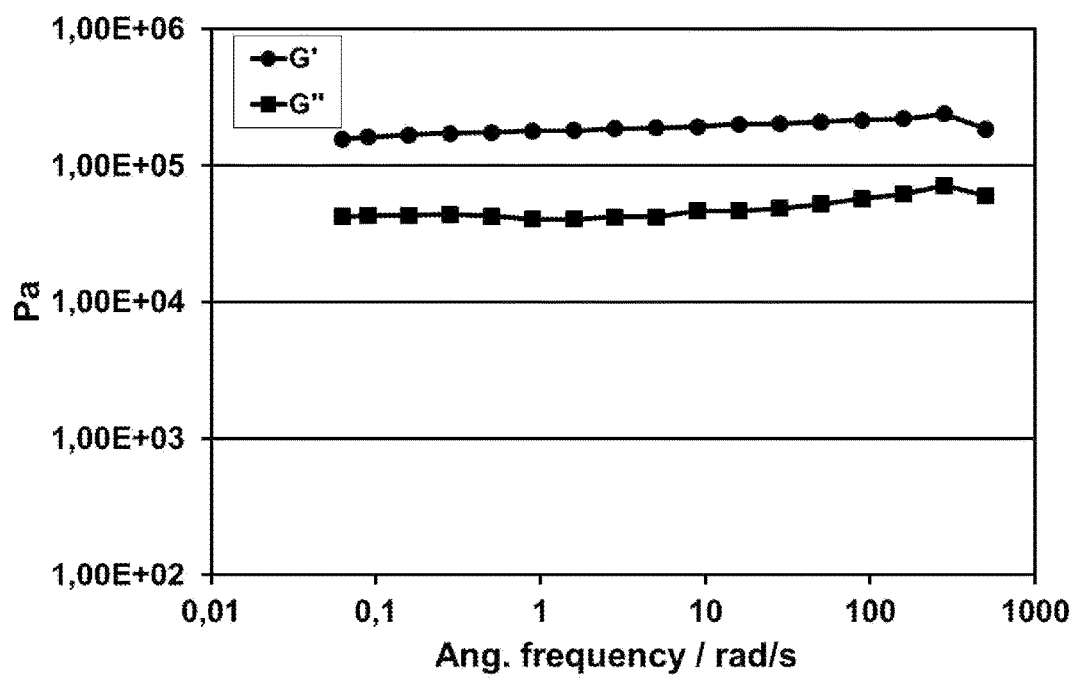

FIG. 18 illustrates elastic (storage) modulus (G') and viscous (loss) modulus (G") for the combined hydrogel composition formed from silica microparticles R4-50 MP (with 30% (w/w) loading of nimodipine) and 2% chitosan sol/solution (the combined hydrogel composition is incubated in 50 mM Tris buffer for 20 hours at 37° C.).

Figure 19:
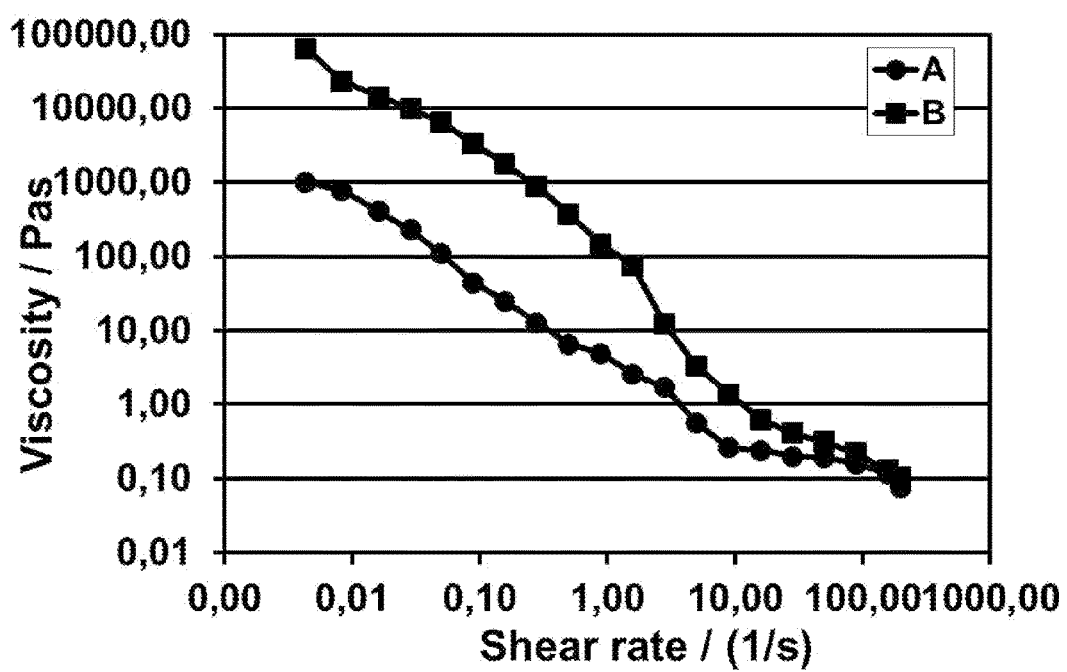

FIG. 19 illustrates dynamic viscosity as a function of shear rate for the combined hydrogel composition formed from silica microparticles R6-50 MP (with 15% (w/w) loading of nimodipine) and silica sol R400 with two different aging times (A=6 hours at room temperature in a syringe, B=1 week in a closed aluminium foil at room temperature).

EXAMPLES

The following experimental section illustrates the invention by providing examples.

Example 1

Preparation of Gel-Like Combined Compositions from Silica Microparticles (MP) and Different Sols or Solutions The sol-gel derived silica microparticles (MP) were prepared using TEOS (tetraethyl orthosilicate=tetraethoxysilane, Sigma-Aldrich) as a precursor for silica. Several microparticle batches with different formulations were prepared with the same general procedure. The initial $R=H_2O/TEOS$ (molar ratio) varied from R4 to R6 and calculated, initial pH in every sample was pH 2 (HCl was used to adjust the pH). The hydrolysis was let to occur at room temperature (at 21-23° C.) for 25 min under continuous mixing prior to pH adjustment of the sol. After hydrolysis the sols were diluted with ethanol to correspond $R=H_2O/TEOS$ between 35 and 50 (same volume of ethanol was used as water is needed to obtain R between 35 and 50 from the initial $R=H_2O/TEOS$ between 4 and 6). For example, a formulation "R4-50 MP" describes a spray-dried silica microparticle formulation where the initial $R=H_2O/TEOS$ (molar ratio) of the silica sol is 4 and after the dilution with ethanol R=35 meaning that the same volume of ethanol is added as water is needed to obtain R=35. Prior to the actual pH adjustment all sols were cooled down to 0° C. in order to avoid the gel formation. The pH was raised to 5.9 by adding 0.1 M NaOH (Merck Titripur®) with continuous stirring for every sample. Every sol was spray-dried to microparticles immediately after the adjustment of the pH by Büchi B-191 spray-dryer (Spray-Dryer parameters: Inlet temperature: 100-120° C.; Outlet temperature: 55-79° C.; Aspirator: 32 m³/h; Feed flow: 3.0 ml/min; Atomization air flow: 600 l/h).

The silica sols (SS) to be mixed with the spray-dried silica microparticles were prepared using TEOS (tetraethyl orthosilicate=tetraethoxysilane, Sigma-Aldrich)) as a precursor. Several different silica sols with $R=H_2O/TEOS$ (molar ratio) between R15 and R500, corresponding to about 12 to 0.65 wt-% of silica, were prepared and calculated, initial pH in every sample was pH 2 (HCl was used to adjust the pH). The hydrolysis was let occur at room temperature (at 21-23° C.) for 25 min under continuous mixing prior to pH adjustment of the sol. The pH was raised to 5.5-5.9 by adding 0.1 M NaOH with continuous stirring. After the pH adjustment the silica sols were immediately mixed with the spray-dried microparticles.

Concentration of the silica microparticles (MP) in the silica sols (SS) varied from 0.1 g/ml to 1.0 g/ml. The formed silica microparticle-silica sol suspensions were transferred into the syringe. The combined compositions of silica microparticles (MP) and silica sols (SS) formed a hydrogel at room temperature and the hydrogel formation time varied from 15 minutes (R15) to 1 week (R400 and R500) depending on the silica sol (SS). The hydrogel formation was slower for the combined compositions than for the silica gels as such and the higher the microparticle concentration the slower the gel formation.

Silica microparticles (MP) were also combined with other materials that resulted in different gel structures. Chitosan sols/solutions were used to form a silica microparticle-chitosan hydrogels and sorbitan monostearate (SMS) was used to form silica microparticle-SMS organogel.

2% (w/v) chitosan hydrogel was prepared by dissolving chitosan (Sigma-Aldrich) into 1% (v/v) acetic acid (Merck) at room temperature. The chitosan solution was cooled down to ca. 0° C. with an ice bath prior to $NaHCO_3$ addition. The concentration of $NaHCO_3$ was adjusted to 0.1 M by adding 1.0 M $NaHCO_3$ solution (Merck). After release of $CO_2$ spray-dried silica microparticles (MP) were suspended into the thick (highly viscous by visual observation) chitosan sol/solution. Concentration of the spray-dried silica microparticles in chitosan sol/solution was 0.5 g/ml. The formed silica microparticle (MP)-chitosan suspension was transferred into the syringe. The combined composition formed a highly viscous sol that did not turn into a before it was transferred into a dissolution medium for the release rate measurements. The said combined composition stays flowing at room temperature for at least 7 days at room temperature in a closed aluminum foil, but turned into a gel in less than 30 minutes when it was injected into a medium that simulates a physiological or body fluid, such as 50 mM Tris buffer at 37° C.

Sorbitan monostearate (SMS, Sigma-Aldrich) and olive oil were used as precursors for an organogel. 2% (w/v) SMS and 15% (w/v) SMS were dissolved into olive oil at 60° C. for 60 min. Prior to cooling and gel formation spray-dried silica microparticles (MP) were suspended into the thick (highly viscous by visual observation) SMS solution. Concentration of the spray-dried silica microparticles was 1.0 g/ml. The formed silica microparticle (MP)-SMS suspension was transferred into the syringe. The combined composition formed an organogel within some hours during the cooling.

It was also tested whether silica microparticles as such form a gel in "a silica sol with 0% of silica", i.e. in water. Two different batches of microparticles (R5-35 with the particle size distribution of 2.80-32.58 μm and R15 with the particle size distribution of 1.82-10.33 μm) prepared by spray-drying were mixed with water (at room temperature (22-23° C.) and pH 6.8) in a concentration of 1 g silica microspheres in 1 ml of water. Neither of these spray-dried silica microparticles (MP) suspensions turned into hydrogel within a month when stored in a syringe in a closed aluminium foil at room temperature (at 22-23° C.).

Example 2

Encapsulation of Nimodipine into the Spray-Dried Silica Microparticles (MP) and Preparation of the Combined Compositions of Said Spray-Dried Microparticles with Silica Sols (SS), Chitosan Solutions and SMS Solutions Nimodipine (Shandong Xinhua Pharmaceutical Co.), a hydrophobic and poorly water-soluble drug molecule (12 μg/ml, DrugBank), with a molecular weight of 418.44, was encapsulated into different formulations of the spray-dried silica microparticles (R4-50 MP, R5-35 MP, R5-50 MP and R6-50 MP). Addition of nimodipine was done into the silica sols that were used to prepare the microparticles. The addition was done after the dilution with ethanol and prior to the cooling, pH adjustment to pH 5.9 and spray-drying. Concentration of nimodipine (loading %) in different microparticle formulations varied from 6 to 30% (w/w meaning the weight ratio between weight of the encapsulated molecule (nimodipine) and the theoretical weight of silica in the formulation).

The spray-dried microparticles (MP) with encapsulated nimodipine were mixed with the silica sols (SS) (R15, R150, R300, R400 and R500) after the pH adjustment to pH 5.5-5.9 and prior to the transfer into the syringe. Concentration of the said spray-dried microparticles (MP) in the silica sols (SS) varied from 0.1 g/ml to 1.0 g/ml. The combined compositions of the said silica microparticles (MP) and silica sols (SS) (R4-50+R150, R5-35+R150, R5-50+R500 and R6-50+R400) formed a gel at room temperature and the gel formation time varied from 15 minutes (R15) to 1 week (R400 and R500) depending on the silica sol (SS) formulation.

The spray-dried silica microparticles with encapsulated nimodipine (R4-50 MP) were also mixed with a 2% (w/v) chitosan solution. Concentration of nimodipine in the spray-dried silica microparticles was 30 wt-% and concentration of the said microparticles in the said chitosan sol/solution was 0.5 g/ml, respectively. The addition of the microparticles into the chitosan sol/solution was done after $CO_2$ release. The chitosan sol/solution is kept in the flowing form by the storing it in cool conditions at room temperature 21-22° C. The formed silica microparticle (MP)-chitosan suspension was transferred into the syringe. The combined composition formed a highly viscous sol that did not turn into a gel before it was transferred into a dissolution medium for the release rate measurements. The said combined composition stays flowing at room temperature for at least 2 months at room temperature in a closed aluminium foil, but turned into a gel in less than 30 minutes when it was injected into a medium that simulates a physiological or body fluid, such as 50 mM Tris buffer at 37° C.

Nimodipine was also directly encapsulated into two different gels, R150 and 2% Chitosan (i.e. encapsulation of nimodipine into plain gels only). Concentration of nimodipine was 45 mg/ml in R150 silica sol and 105 mg/ml in 2% Chitosan sol/solution, respectively. The concentrations of nimodipine were the same as the amount of nimodipine in the corresponding combined compositions with the spray-dried silica microparticles and sols/solutions. Nimodipine was added after the pH adjustment of the R150 silica sol and after $NaHCO_3$ addition in the chitosan solution and prior to the gel formation. The formed mixtures of nimodipine-silica sol and nimodipine-chitosan sol/solution were transferred into the syringe. R150 silica sol with nimodipine turned in to a gel within 1.5-2 hours and the chitosan sol/solution formed a highly viscous sol that did not turn into a gel before it was transferred into a dissolution medium for the release rate measurements. The said chitosan composition stays flowing at room temperature for at least 7 days at room temperature in a closed aluminium foil, but turned into a gel in less than 30 minutes when it was injected into a medium that simulates a physiological or body fluid, such as 50 mM Tris buffer at 37° C.

Example 3

Encapsulation of Fluorescein into the Spray-Dried Silica Microparticles (MP) and Preparation of the Combined Compositions of Said Spray-Dried Microparticles with Silica Sols (SS), Chitosan Solutions and SMS Solutions Fluorescein (Sigma-Aldrich), a hydrophilic and highly water-soluble model molecule (800 μg/ml), with a molecular weight of 332.31, was encapsulated into the spray-dried silica microparticles (R5-50 MP). Addition of fluorescein was done into the silica sols that were used to prepare the spray-dried silica microparticles. Addition of fluorescein was done into the sols after the dilution and prior to the cooling, pH adjustment to pH 5.9 and spray-drying. The concentration (loading %) of fluorescein in the spray-dried silica microparticles was 15% (w/w meaning the weight ratio between the weight of the encapsulated molecule (fluorescein) and the theoretical weight of silica in the formulation). The spray-dried silica microparticles (MP) were then mixed with a silica sol (SS, R150) after pH adjustment to pH 5.9 and prior to transfer into the syringe. Concentration of the said spray-dried silica microparticles in the silica sol was 1.0 g/ml. The combined composition formed a gel at room temperature (at 21-23° C.) within 18-20 (overnight) hours The said spray-dried silica microparticles (R5-50 MP) were also mixed with a 2% chitosan solution. The concentration of fluorescein in the spray-dried silica microparticles was 15 wt-% and concentration of the said microparticles in the 2% chitosan solution was 0.5 g/ml, respectively. Addition of microparticles was done after $CO_2$ release and prior to gel formation. The formed silica microparticle (MP)-chitosan suspension was transferred into the syringe. The combined composition formed a highly viscous sol that did not turn into a gel before it was transferred into a dissolution medium for the release rate measurements. The said combined composition stays flowing at room temperature for at least 7 days at room temperature in a closed aluminum foil, but turned into a gel in less than 30 minutes when it was injected into a medium that simulates a physiological or body fluid, such as 50 mM Tris buffer at 37° C.

The said spray-dried silica microparticles (R5-50 MP) were also mixed with 2% SMS and 15% SMS solutions. The concentration of fluorescein in the spray-dried silica microparticles was 15 wt-% and concentration of microparticles in the SMS solutions was 1.0 g/ml, respectively. The microparticles were mixed with a warmed solution 60° C. and prior to the gel formation. The formed silica microparticle (MP)-SMS suspension was transferred into the syringe. The combined composition formed a gel within some hours during the cooling.

Fluorescein was also directly encapsulated into four different gels; R150 silica hydrogel, 2% chitosan hydrogel, 2% SMS and 15% SMS organogels, in other words, fluorescein was encapsulated into plain gels only. Concentration of fluorescein was 52.5 mg/ml in 2% Chitosan hydrogel and 105 mg/ml in R150, 2% SMS and 15% SMS gels, respectively. The concentrations of fluorescein were the same as the amount of nimodipine in the corresponding combined gel compositions of the spray-dried silica microparticles and sols/solutions. Fluorescein was added into sols/solutions after pH adjustment (R150 silica hydrogel) or after $NaHCO_2$ addition (the organic hydrogel, i.e., chitosan) or into the warmed solution (organogels) prior to the gel formation. The formed mixtures of fluorescein-sol/solutions were transferred into the syringe. The combined compositions turned into gels either spontaneously (R150 and organogels) or as transferred into a dissolution medium for the release rate measurements (chitosan hydrogel).

Example 4

The Burst of Nimodipine from Hydrogels, Silica Microparticles and their Combined Compositions Hydrogels, silica microparticles (MP) and combined compositions of the hydrogels and silica microparticles (formulations and compositions are shown in table 1) with encapsulated nimodipine were studied by immersing them in 50 mM Tris+0.1% (w/v) sodium dodecylsulphate (SDS, Sigma-Aldrich) buffer solution (pH 7.4 at 37° C.) to study the burst in sink conditions (at $c(SiO_2)$<30 ppm, i.e. at $c(SiO_2)$ that is less than 20% of the solubility of the particular $SiO_2$ at the same conditions). In the combined compositions nimodipine is encapsulated only in the silica microparticles. The concentrations of nimodipine at different time points were detected with a high pressure liquid chromatography (HPLC-UV). The chromatographic separation was obtained on a Gemini 5μ C18 110 A, 150×2.0 mm (Phenomenex, or equal) analytical HPLC column. The mobile phase consisted of a mixture of acetonitrile and 15 mM hydrogen phosphate-buffer (60:40 v/v). The release of nimodipine from different compositions is shown in FIGS. 2-8 as cumulative release of nimodipine. R150 silica gel was in the form of a gel when immersed into the dissolution medium, but the chitosan solution/sol turned into a gel after being injected into the dissolution medium. The aging times (time from the preparation of the sols/solutions until the start of the release rate measurement) of the gels and sols/solutions are given in table 2. Thus, all the studied materials were in the form of a gel). The burst (results in table 2) decreased with all combined compositions compared with silica or chitosan hydrogels or silica microparticles. The combined gel structure formed from R5-50 MP and R500 silica sol (the silica sol with lowest silica dry content in this example) decreased the burst only a little compared with the other corresponding combined composition.

TABLE 1

Burst of Nimodipine from hydrogels and silica microparticles (MP)

| Composition | c (nimodipine) | Burst |
|---|---|---|
| R150 silica gel | 45 mg/ml | 13.0% |
| 2% Chitosan gel | 105 mg/ml | 1.7% |
| R4 - 50 MP | 30 wt - % (vs. $SiO_2$) | 30.3% |
| R5 - 35 MP | 6 wt - % (vs. $SiO_2$) | 10.2% |
| R5 - 50 MP | 15 wt - % (vs. $SiO_2$) | 42.0% |
| R6 - 50 MP | 15 wt - % (vs. SiO2) | 24.3% |

The burst of nimodipine was also measured by using a flow-through dissolution method for two different formulations; for silica microparticles (R5-35 MP) and for the combined hydrogel composition formed from the silica microparticles R5-35 MP and silica sol R150. In the flow-through dissolution method the microparticles and the combined hydrogel composition were transferred into sample container with 150 ml of 50 mM Tris+0.1% (w/v) SDS buffer solution (pH 7.4 at 37° C.) and the dissolution medium was changed continuously by pumping it through sample container at the flow rate of 347 μl/in (ca. 500 ml/day). The burst of nimodipine from silica compositions are shown in FIG. 9 (A=R5-35 MP with 6% of nimodipine loading and B=R5-35 MP+R150). The burst from the combined hydrogel composition was minimal compared with the burst from the silica microparticles.

TABLE 2

Burst of Nimodipine from combined hydrogel

| Combined composition | Aging time | c (microparticles) | c (nimodipine) | Burst |
|---|---|---|---|---|
| R6-50 MP + R100 silica sol | 1 day | 1.0 g/ml sol | 15 wt-% (vs. $SiO_2$) | 1.5% |
| R5-35 MP + R150 silica sol | 1 day | 1.0 g/ml sol | 6 wt-% (vs. $SiO_2$) | 4.1% |
| R4-50 MP + R150 silica sol | 1 day | 0.5 g/ml sol | 30 wt-% (vs. $SiO_2$) | 3.0% |
| R5-50 MP + R300 silica sol | 3 days | 1.0 g/ml sol | 15 wt-% (vs. $SiO_2$) | 7.5% |
| R6-50 MP + R400 silica sol | 1 week | 1.0 g/ml sol | 15 wt-% (vs. $SiO_2$) | 5.6% |
| R5-50 MP + R500 silica sol | 1 week | 1.0 g/ml sol | 15 wt- (vs. $SiO_2$) | 30.9% |
| R4-50 MP + 2% chitosan | 1 day | 0.5 g/ml sol/solution | 30 wt-% (vs. $SiO_2$) | 0.03% |

Example 5

The Burst of Fluorescein from Gels, Silica Microparticles and their Combined Compositions Hydrogels, organogels, silica microparticles and their combined compositions with encapsulated fluorescein were studied by immersing them in 50 mM Tris buffer solution (pH 7.4 at 37° C.) for burst of fluorescein measurements in sink conditions [$c(SiO_2)$<30 ppm, i.e., at $c(SiO_2)$ that is less than 20% of the solubility of the particular $SiO_2$ at the same conditions]. In the combined compositions fluorescein is encapsulated only in the silica microparticles. The fluorescein concentrations at different time points were measured with a spectrophotometer (Jasco V-560) analyzing the absorbance at 452 nm. The burst results of fluorescein from different silica compositions are shown in FIG. 10 (A=R150 silica hydrogel, B=R5-50 MP silica microparticles and C=combined hydrogel composition formed from R5-50 MP silica microparticles+R150 silica sol) as cumulative releases of fluorescein. The burst of fluorescein was highest for R150 silica hydrogel (66.1%), lower for R5-50 MP (11.3%) and lowest for the combined hydrogel composition R5-50 MP+R150 (5.3%). The burst-% was calculated from total amount of fluorescein encapsulated in each formulation.

The burst of fluorescein from 2% Chitosan hydrogel was lower than from the silica microparticles but higher than from the combined hydrogel composition. The burst results are shown in FIG. 11 (A=2% chitosan hydrogel, B=R5-50 MP silica microparticles and C=combined hydrogel composition formed from R5-50 MP silica microparticles+2% chitosan sol/solution). The burst of fluorescein from chitosan hydrogel was 6.7%, 11.3% from R5-50 MP silica microparticles and 2.8%, from the combined hydrogel composition formed from R5-50 MP silica microparticles+2% chitosan sol/solution, respectively. The burst from the chitosan hydrogel as such was relatively low, but the release was otherwise faster than from the silica microparticles and the combined hydrogel compositions. The clearly lowest burst, however, was that of the combined hydrogel composition.

The burst of fluorescein from the both prepared organogel formulations were very high (59.8% from 2% SMS sol and 59.1% from 15% SMS gel). 15% SMS organogel formulation formed a gel during the cooling in the end of the preparation process, but 2% SMS formulation did not form a gel, it was in the form of a viscous, slowly flowing sol. The aging time of the organogel formulations was 1 day before they were immersed into the dissolution medium for the burst and release rate measurements. When the organogel formulation were combined with the silica microparticles, the resulting combined organo compositions did not decrease the burst at all when compared with the burst from the silica microparticles R5-50MP. The results are shown in FIG. 12. The burst of fluorescein was on the same level or even higher from the combined organogel compositions, 11.3% from the R5-50 MP silica microparticles, 13.7% from the combined composition formed from R5-50 MP silica microparticles+2% SMS and 17.5% from the combined composition formed from R5-50+15% SMS.

Example 6

The Burst of Fluorescein from Silica Microparticles and from the Combined Flowing Composition of a Silica Sol and Silica Microparticles In order to study whether the hydrogel morphology as such is of importance with respect to the burst, 2 different combined flowing compositions formed from R15 silica sol and silica microparticles R5-50 with 15% (w/w) loading of fluorescein were prepared. The silica microparticles R5-50 MP with the encapsulated fluorescein were combined with the R15 silica sol in 2 different concentrations (0.1 g of silica microparticles/ml of silica sol and 0.5 g of silica microparticles/ml of silica sol). The prepared silica sol formulation (R15) has a higher solid content than the sols used in the preparation of the combined hydrogel compositions in other examples (R100-500), because it can be expected than if a flowing sol would affect the burst, it is more likely with a silica sol with a higher solid content of silica. The results in FIG. 13 show, however, that the silica sols do not affect the burst at all. The burst from the R5-50 MP silica microparticles with the encapsulated fluorescein was 11.3%, 16.5% when the said silica microparticles were combined with the R15 silica sol in the concentration of 0.1 mg/ml and 14.7% when the said silica microparticles were combined with the R15 silica sol in the concentration of 0.5 mg/ml. Thus, the results of this example combined with the results on the hydrogels in the examples 4 and 5 show that a non-flowing structure, e.g., a hydrogel is needed in order to decrease the burst from the silica microparticles.

Example 7

Particle Size Distribution of Silica

The Particle Size Distribution was determined using Malvern Mastersizer MicroPlus particle size analyser (Malvern Instruments). The particles were dispersed in isooctane using 4% (v/v) Span™ as a dispersant. The equipment was left to warm up for about 1 hour and approximately 100 ml of the dispersion medium (isooctane with 4% Span™) was added into the sample dispersion unit. Backgrounds were first measured using for the dispersion medium. A fresh sample was prepared by adding ca. 50 mg of silica microparticles into 2 ml of the dispersion medium and the mixture was sonicated (ultrasound treatment) for ca. 1 min. The mixture was added drop-wise into the sample dispersion unit under stirring until a suitable obscuration value (i.e. 16-25%) was achieved and the particle size distribution could be measured. A minimum of three measurements were made for each sample over a 5 minute period to confirm that the particle size distribution and obscuration remained constant (i.e. the silica microparticles were not dissolving but stayed well dispersed in the dispersion medium).

The results are summarised in the table 3 below (averages of three measurements).

TABLE 3

| Microparticle formulation | Average D10 (µm) | Average D50 (µm) | Average D90 (µm) |
|---|---|---|---|
| R4 - 50 MP | 6.25 | 28.85 | 100.52 |
| R5 - 35 MP | 2.80 | 14.85 | 32.58 |
| R5 - 50 MP | 6.41 | 29.52 | 148.32 |
| R6 - 50 MP | 4.11 | 18.85 | 47.68 |

Example 8

Rheological Measurements for Silica Microparticle Suspensions, Silica Sols and Gels and for Combined Compositions of Silica Microparticles and Gels and Sols and the Relationships Between the Combined Hydrogel Structures and the Release of Encapsulated Nimodipine Rheological measurements were conducted with a rheometer (AR 2000 Ex, with a plastic plate measuring head with the diameter of 60 mm, TA instruments, Germany) to measure elastic and viscous modulus and dynamic viscosity for the different compositions. FIGS. 14, 15 and 16 show the elastic and viscous moduli for the combined hydrogel compositions formed from silica microparticles and silica sols. The combined hydrogel compositions in FIGS. 14 and 15 are both examples on the all-silica hydrogel structures that reduce the burst clearly. The elastic modulus for the combined hydrogel composition formed from silica microparticles R5-35 MP [with 6% (w/w) loading of nimodipine] and silica sol R150 in (aged for 1 day at room temperature in a closed aluminium foil package) FIG. 14 is on the level of 14 kPa with different angular radii in the oscillatory measurements. The elastic moduli indicate a relatively loose hydrogel structure, but the effect on the burst was clear (the burst results for the same combined hydrogel composition are in table 2 and FIG. 3). The elastic modulus for the combined hydrogel composition (aged for 1 week at room temperature in a closed aluminium foil package) formed from silica microparticles R6-50 MP [with 15% (w/w) loading of nimodipine] and silica sol R400 in FIG. 15 is even lower, on the level of 4 kPa indicating another loose hydrogel structure that reduced the burst remarkably compared with the silica microparticles as such (the burst results for the corresponding combined hydrogel composition are shown in table 2 and FIG. 6. The elastic and viscous moduli (shown in FIG. 16) for the same combined hydrogel composition {formed from R6-50 MP [with 15% (w/w) loading of nimodipine] and silica sol R400} measured right after the combination of the silica sol and the silica microparticles as the combined composition has turned into a hydrogel are even lower indicating a hydrogel structure but also evolution of the hydrogel structure within 1 day of aging. However, the combined hydrogel composition {formed from R6-50 MP [with 15% (w/w) loading of nimodipine] and silica sol R400} aged for 1 day at room temperature in a closed aluminium foil package is still easy to inject with thin needles like 18-25 G, i.e., the relatively loose hydrogel structure turns into flowing form and regels again after the injection, and the resulting hydrogel decreases the burst clearly.

The elastic and viscous moduli (in FIG. 17) for a combined flowing composition of R15 silica sol+R5-50 MP with 15% (w/w) loading of fluorescein and with the silica microparticle concentration of 0.1 g/ml show that the combined composition has not turned into a gel (the viscous modulus is higher than the elastic modulus). The correlation to the burst and release results is also clear, the flowing combined composition did not affect in practice the burst and the overall release rate at all as shown in FIG. 13. Thus, a hydrogel structure is needed for the all-silica systems in order to affect the burst.

The elastic and viscous moduli for a combined hydrogel composition formed from silica microparticles R4-50 MP [with 30% (w/w) loading of nimodipine] and 2% chitosan sol/solution [corresponds to R150 silica sol, where the dry content of silica is about 2.05%] are shown in FIG. 18. The said combined composition stays flowing for at least 7 days at room temperature in a closed aluminium foil, but turned into a gel in less than 30 minutes when it was injected into a medium that simulates a physiological or body fluid, such as 50 mM Tris buffer at 37° C. Prior to the oscillatory measurements, the combined hydrogel composition is incubated in 50 mM Tris buffer for 20 hours at 37° C. in order to characterize the materials properties of the combined hydrogel composition during the release studies. The elastic modulus is clearly higher (ca. 200 kPa) than that of all-silica structures (results in FIGS. 14 and 15) indicating a stiffer gel structure. When compared with the corresponding all-silica system (a combined hydrogel structure formed from R5-35 MP and silica sol R150 (with ca. 2% of silica) that has been aged 1 day at room temperature in a closed aluminium foil, the elastic modulus is ca. 14 times lower for the all-silica structure. The stiffer hydrogel structure (formed from R4-50 MP [with 30% (w/w) loading of nimodipine] and 2% chitosan sol/solution) decrease the burst very well, but it also slows down the overall release of the encapsulated nimodipine clearly as shown in FIG. 8. The overall decrease of the release rate is remarkable although the loading-% of nimodipine is 30% in the silica microspheres. However, for the combined hydrogel structure formed from R5-35 MP and silica sol R150 (with ca. 2% of silica) only the burst is affected or the overall release is changed only a little as shown in FIG. 3 (corresponding results for the other silica formulations are shown, e.g. in FIGS. 2, 4, 5, 6 and 7). This is a potential advantage for the combined all-silica hydrogel structures, because the overall release rate of nimodipine and other encapsulated molecules can be adjusted on a large scale based on the silica microparticle formulations only. When only the burst is affected in the combined all-silica hydrogel structures, the overall release rate is still based on silica microparticle formulations. The corresponding chitosan-based release system is more complicated to control, because the hydrogel structure affects (slows down) remarkably both the burst and the overall release rate. When this is combined with the fact that the all-silica hydrogel systems can be stored as hydrogels (ensures the homogeneous distribution of the encapsulated agents, which is not sure in viscous systems that are always more or less flowing) and they turn into a flowing form when injected {this shear-thinning behaviour is illustrated for the combined hydrogel composition formed from silica microparticles R6-50 MP [with 15% (w/w) loading of nimodipine] in FIG. 19} with thin needles like 18-25 G and regel again after injection, it can be said that the all-silica hydrogel structures are easier to design with respect to the use and controlled release.

OTHER PREFERRED EMBODIMENTS

It will be appreciated that the composites and methods of the present invention can be incorporated in the form of a variety of embodiments, only a few of which are disclosed herein. It is e.g. apparent for the expert skilled that embodiments of the composites and methods have corresponding method and composite, respectively, embodiments. It will be apparent for the expert skilled in the field that other embodiments exist and do not depart from the spirit of the invention. Thus, the described embodiments are illustrative and should not be construed as restrictive.

The invention claimed is:

1. A silica hydrogel composite obtained by mixing
   a) silica microparticles, comprising an encapsulated agent other than the silica itself and having a diameter between 1 μm and 300 μm, as such or as a suspension, with
   b) a silica sol comprising solid particles ≤50 nm; wherein
   i) said silica sol has a solid content of ≤5 wt-%,
   ii) said silica hydrogel composite comprises up to 85 wt-% of said silica microparticles, and
   iii) said hydrogel composite is shear-thinning.

2. The silica hydrogel composite of claim 1 wherein the silica sol has a solid content of ≤3 wt-%.

3. The silica hydrogel composite of claim 1 wherein the silica microparticles comprise from 0.1 to 70 wt-% of the encapsulated agent.

4. The silica hydrogel composite of claim 1, wherein the hydrogel composite comprises from up to 80 wt-% of the silica microparticles.

5. The silica hydrogel composite of claim 1, wherein the composite solid content is from 20 wt-% to 75 wt-%.

6. The silica hydrogel composite of claim 1, wherein the elastic modulus measured under small angle oscillatory shear in the linear viscoelastic region is <300 kPa.

7. The silica hydrogel composite of claim 1, wherein the encapsulated agent is fluorescein.

8. The silica hydrogel composite of claim 1, wherein the encapsulated agent is a biologically active agent.

9. The silica hydrogel composite of claim 8 characterized in that biologically active agent is an active pharmaceutical ingredient, API.

10. The silica hydrogel composite of claim 9 characterized in that the API is nimodipine.

11. The silica hydrogel composite according to claim 1, wherein the water solubility of the encapsulated agent is ≤10 mg/ml.

12. The silica hydrogel composite of claim 1, wherein the molecular weight of the encapsulated agent is ≤10 000.

13. The silica hydrogel composite of claim 1, wherein the silica microparticles are selected from the group consisting of spray dried silica microparticles, silica fibre fragments, molded silica monoliths, cast silica monoliths and crushed silica monoliths.

14. A method of administering an encapsulated agent to a patient in need of said agent, said method comprising
   providing the silica hydrogel composite of claim 1, and administering said composite to said patient.

15. The method of claim 14 wherein said composite is administered to said patient by parenteral injection or by implantation.

16. The method of claim 15 wherein administration is parenteral and selected from the group consisting of intravenous, intraarterial, intracardiac, topical, transdermal, intradermal, subcutaneous, intramuscular, intraperitoneal, intracerebral, intracerebroventricular, intrathecal, intraosseous, intraarticular, intraocular, intrasternal, intravesical and intracavernosal.

17. A method for preparing a silica hydrogel composite comprising
   mixing silica microparticles, comprising a biologically active agent other than the silica itself and having a diameter between 1 μm and 300 μm, as such or as a suspension, with a silica sol; wherein
i) said silica sol has a solid content of ≤5 wt-% and comprises solid particles ≤50 nm,
ii) said hydrogel composite comprises up to 85 wt-% of said silica microparticles, and
iii) said hydrogel composite is shear-thinning.

18. The method of claim 17 wherein the silica sol has a solid content of ≤3 wt-%.

19. The method of claim 17 wherein the silica microparticles comprise from 0.1 to 70 wt-% of the encapsulated agent.

20. The method of claim 17, wherein the hydrogel composite comprises up to 80 wt-% of the silica microparticles.

21. The method of claim 17, wherein the composite solid content is from 20 wt-% to 75 wt-%.

22. The method according to claim 17, wherein the silica microparticles are prepared by a sol-gel process.

23. The method of claim 17, wherein the silica microparticles are selected from the group consisting of spray dried silica microparticles, silica fibre fragments, molded silica monoliths, cast silica monoliths and crushed silica monoliths.

* * * * *